United States Patent
Wang et al.

(10) Patent No.: US 12,230,386 B2
(45) Date of Patent: Feb. 18, 2025

(54) HEALTH MANAGING METHOD AND STORAGE MEDIUM

(71) Applicant: BOE TECHNOLOGY GROUP CO., LTD., Beijing (CN)

(72) Inventors: Yunan Wang, Beijing (CN); Yongyang Yan, Beijing (CN); Yuan Li, Beijing (CN); Hua Bai, Beijing (CN); Hao Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 716 days.

(21) Appl. No.: 17/350,156

(22) Filed: Jun. 17, 2021

(65) Prior Publication Data
US 2022/0037002 A1 Feb. 3, 2022

(30) Foreign Application Priority Data
Jul. 31, 2020 (CN) .......................... 202010761400.X

(51) Int. Cl.
*G16H 40/20* (2018.01)
*A61B 5/00* (2006.01)
(Continued)

(52) U.S. Cl.
CPC ............. *G16H 40/20* (2018.01); *A61B 5/746* (2013.01); *G06F 16/2455* (2019.01); (Continued)

(58) Field of Classification Search
CPC ........ G16H 50/30; G16H 50/20; G16H 20/30; G16H 40/67; G16H 15/00; G16H 80/00; G16H 10/60
See application file for complete search history.

(56) References Cited

U.S. PATENT DOCUMENTS

2006/0235280 A1* 10/2006 Vonk ...................... G16H 50/20
600/300
2007/0185391 A1* 8/2007 Morgan ............... A61B 5/0002
128/920
(Continued)

FOREIGN PATENT DOCUMENTS

| CN | 107229814 A | 10/2017 |
| CN | 107491651 A | 12/2017 |

(Continued)

OTHER PUBLICATIONS

J. C. C. Tseng et al., "An interactive healthcare system with personalized diet and exercise guideline recommendation," 2015 Conference on Technologies and Applications of Artificial Intelligence (TAAI), Tainan, Taiwan, 2015, pp. 525-532, doi: 10.1109/TAAI.2015.7407106 (Year: 2015).*

(Continued)

*Primary Examiner* — Joseph D Burgess
(74) *Attorney, Agent, or Firm* — Dilworth & Barrese, LLP.; Michael J. Musella, Esq.

(57) ABSTRACT

A health managing method, a computing device and a storage medium are disclosed. The health managing method includes: connecting to an object information database, and acquiring at least one piece of physical sign data of an object from the object information database, wherein the at least one piece of physical sign data includes an examination result of at least one physical sign examination item in which the object participates; automatically determining at least a health management influencing factor at least based on the at least one piece of physical sign data; and automatically generating a coping approach recommendation form at least based on the health management influencing factor, wherein the coping approach recommendation form is used to generate a coping approach suggestion form.

17 Claims, 32 Drawing Sheets

(51) Int. Cl.
  *G06F 16/2455* (2019.01)
  *G16H 10/20* (2018.01)
  *G16H 10/60* (2018.01)
  *G16H 15/00* (2018.01)
  *G16H 20/10* (2018.01)
  *G16H 20/30* (2018.01)
  *G16H 20/60* (2018.01)
  *G16H 40/67* (2018.01)
  *G16H 50/30* (2018.01)
  *G16H 50/70* (2018.01)
  *G16H 70/40* (2018.01)
  *G16H 10/40* (2018.01)

(52) U.S. Cl.
  CPC ............ *G16H 10/20* (2018.01); *G16H 10/60* (2018.01); *G16H 15/00* (2018.01); *G16H 20/10* (2018.01); *G16H 20/30* (2018.01); *G16H 20/60* (2018.01); *G16H 40/67* (2018.01); *G16H 50/30* (2018.01); *G16H 50/70* (2018.01); *G16H 70/40* (2018.01); *G16H 10/40* (2018.01)

(56) References Cited

U.S. PATENT DOCUMENTS

| | | | |
|---|---|---|---|
| 2009/0076857 A1* | 3/2009 | Eletreby | G16H 70/40 |
| | | | 705/2 |
| 2011/0046972 A1* | 2/2011 | Leverette | G16H 50/30 |
| | | | 705/2 |
| 2017/0262604 A1* | 9/2017 | Francois | G16H 10/60 |
| 2024/0087700 A1* | 3/2024 | Gnanasambandam | |
| | | | G16H 50/20 |

FOREIGN PATENT DOCUMENTS

| | | |
|---|---|---|
| CN | 108334731 A | 7/2018 |
| CN | 109102855 A | 12/2018 |
| CN | 109411091 A | 3/2019 |
| CN | 110289101 A | 9/2019 |
| CN | 110491526 A | 11/2019 |
| CN | 110767278 A | 2/2020 |
| CN | 110808087 A | 2/2020 |

OTHER PUBLICATIONS

Chinese Office Action from Application No. 202010761400.X; Mailing Date : May 21, 2024.

* cited by examiner

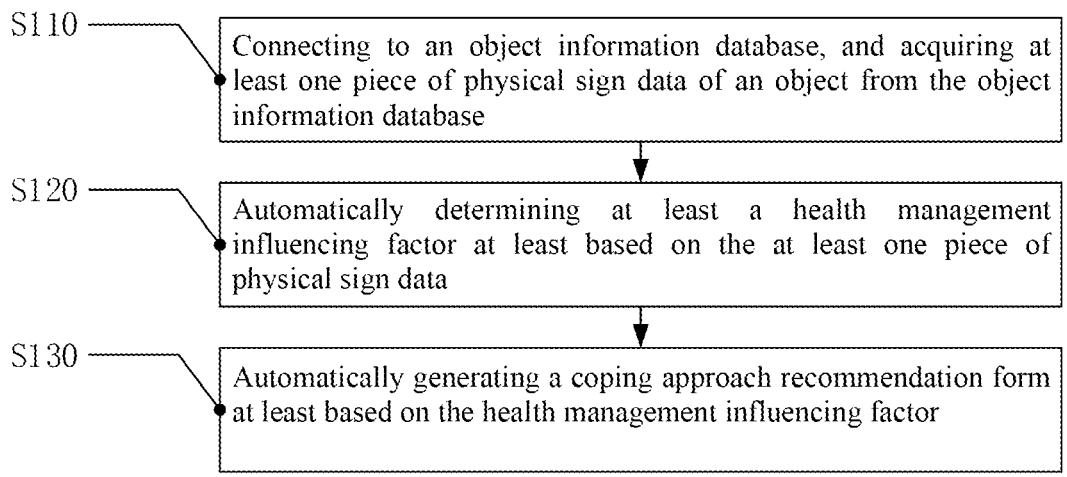

S110 — Connecting to an object information database, and acquiring at least one piece of physical sign data of an object from the object information database S120 — Automatically determining at least a health management influencing factor at least based on the at least one piece of physical sign data S130 — Automatically generating a coping approach recommendation form at least based on the health management influencing factor

FIG. 1

Physical sign examination report list

| Name | Institution | Time | Operation |
|---|---|---|---|
| Name1 | Institution1 | 2019-11-09 00:00:00 | View details |
| Name2 | Institution2 | 2019-11-07 00:00:00 | View details |
| Name3 | Institution3 | 2019-11-05 00:00:00 | View details |
| Name4 | Institution4 | 2019-11-04 00:00:00 | View details |
| Name5 | Institution5 | 2019-11-02 00:00:00 | View details |
| Name6 | Institution6 | 2019-07-11 00:00:00 | View details |
| Name7 | Institution7 | 2019-07-11 00:00:00 | View details |
| Name8 | Institution8 | 2018-11-07 00:00:00 | View details |

FIG. 2A

| Influencing factors | | | Cardiovascular grade stratification | Medium risk |
|---|---|---|---|---|
| | Current value | | Hypertension grade | |
| Blood pressure | | | Select | |

Risk factors

| ☐ SBP140-159and(or)DBP90-99 | ☐ SBP160-179and(or)DBP100-109 | ☐ SBP≥180and(or)DBP≥110 |
|---|---|---|
| ☐ Factor 4 | ☐ Factor 5 | ☐ Factor 6 |
| ☐ Factor 8 | ☐ Factor 9 | |
| ☐ Factor 10 | | |
| ☐ Factor 11 | | ☐ Factor 12 |
| ☐ Factor 13 ☐ Factor 14 | | |

Target cell injuries

| ☐ Injury 1 | ☐ Injury 6 | |
|---|---|---|
| ☐ Injury 2 | | |
| ☐ Injury 3 | | ☐ Injury 7 |
| ☐ Injury 4 | ☐ Injury 8 | |
| ☐ Injury 5 | | |

FIG. 2B

| | | | | |
|---|---|---|---|---|
| Monday | Peanut buns, soy milk and boiled eggs | Recipe 12 | Recipe 13 | |
| Tuesday | Recipe 21 | Recipe 22 | Recipe 23 | |
| Wednesday | Recipe 31 | Recipe 32 | Recipe 33 | |
| Thursday | Recipe 41 | Recipe 42 | Recipe 43 | |
| Friday | Recipe 51 | Recipe 52 | Recipe 53 | |
| Saturday | Recipe 61 | Recipe 62 | Recipe 63 | |

FIG. 3

| Week | Exercise item | Duration each time | Consumption | Operation |
|---|---|---|---|---|
| Monday | Walk: 4.0 km/h, downhill | 30 | 108 | |
| | Stretch: slow and soft | 10 | 26 | |
| | Aerobics class | 30 | 255 | |
| Tuesday | Ride: 19.3-22 km/h | 25 | 217.49999999999997 | |
| | Stretch: slow and soft | 10 | 26 | |
| Wednesday | Fast walk exercise: 6.4 km/h | 35 | 189 | |
| | Static hip bridge | 10 | 38 | |
| | Stretch: slow and soft | 10 | 26 | |
| Thursday | Rest | | 0 | |
| Friday | Leisure walk | 60 | 190 | |
| | Stretch: slow and soft | 10 | 26 | |

First page > Entry admin

Doctor XX, welcome!  Quit  Reset password  Help

| ID | Drug name | Times per day | Dose per day | Category | Operation |
|---|---|---|---|---|---|
| 830 | Drug 1 | 1 piece per day—1 piece every 2 to 3 days | 1 piece | System | Edit |
| 829 | Drug 2 | 3 | 1 to 4 pieces | System | Edit |
| 828 | Drug 3 | 1 | 1 piece | System | Edit |
| 827 | Drug 4 | 1 | 1 piece | System | Edit |
| 826 | Drug 5 | 1 | 1 piece | System | Edit |
| 825 | Drug 6 | ? | 30 to 60 mg | System | Edit |
| 824 | Drug 7 | | | | |

Drug name: Enter name  Inquire

Drug entry | Supervision entry

Chronic Disease Management System

- Patient admin
- Data statistics
- Entry admin
- Health supervision
- Account setting

| ID | Drug name | Times per day | Dose per day | Category | Operation |
|---|---|---|---|---|---|
| 830 | Drug 1 | 1 piece per day---1 piece every 2 to 3 days | 1 piece | System | Edit |
| 829 | Drug 2 | 3 | 1 to 4 pieces | System | Edit |
| 828 | Drug 3 | 1 | 1 piece | System | Edit |
| 827 | Drug 4 | 1 | 1 piece | System | Edit |
| 826 | Drug 5 | 1 | 1 piece | System | Edit |
| 825 | Drug 6 | 3 | 30 to 60 mg | System | Edit |
| 824 | Drug 7 | | | | |

First page > Order admin

| No. | Order-paid time | Package name | Chronic Disease type | Purchasing customer | VIP grade | Health concern | Gender | Unit | Abnormal contents | Transaction amount | Manager |
|---|---|---|---|---|---|---|---|---|---|---|---|
| 1 | 2020-06-04 10:24:18 | Hypertension package | Hypertension | Object 1 | 3 | 2 | Female | | Hypertension Grade 1 | 27946 | Manager 1.5 |
| 2 | 2020-06-03 14:10:48 | Hypertension package | Hypertension | Object 2 | 3 | 3 | Male | | Hypertension | 23412 | Manager 1.5 |
| 3 | 2020-06-03 14:16:48 | Hypertension package | Hypertension | Object 3 | 3 | 3 | Male | | Hypertension | 46617 | Manager 1.3 |
| 4 | 2020-06-03 11:10:31 | Advanced hypertension package | Hypertension | Object 4 | 3 | 1 | Female | | Hypertension Grade 2 | 32734 | Manager 1.3 |
| 5 | 2020-06-04 14:10:48 | Hypertension package | Hypertension | Object 5 | 3 | 3 | Male | | Hypertension Grade 1 | 77108 | Manager 1.1 |
| 6 | 2020-06-03 14:10:48 | Hypertension package | Hypertension | Object 6 | 3 | 3 | Male | | Hypertension | 23695 | Manager 1.3 |
| 7 | 2020-06-04 10:24:18 | Hypertension package | Hypertension | Object 7 | 2 | 2 | Female | | Hypertension Grade 1 | 19812 | Manager 1.5 |
| 8 | 2020-06-04 10:24:18 | Hypertension package | Hypertension | Object 8 | 2 | 2 | Female | | Hypertension Grade 1 | 79480 | Manager 1.1 |
| 9 | 2020-06-03 11:10:31 | Advanced hypertension package | Hypertension | Object 9 | 3 | 1 | Female | | Hypertension Grade 2 | 88314 | Manager 1.1 |
| 10 | 2020-06-04 10:24:18 | Hypertension package | Hypertension | Object 10 | 2 | 2 | Female | | Hypertension Grade 1 | 92457 | Manager 1.5 |

FIG. 27

HEALTH MANAGING METHOD AND STORAGE MEDIUM

CROSS-REFERENCE TO RELATED APPLICATIONS

The application claims priority to Chinese patent application No. 202010761400.X, filed on Jul. 31, 2020, the entire disclosure of which is incorporated herein by reference as part of the present application.

TECHNICAL FIELD

Embodiments of the present disclosure relate to a health managing method and a storage medium.

BACKGROUND

With economic development and improvement of living standards, more and more people suffer from chronic disease of varying degrees. Common chronic disease (or non-communicable disease) mainly includes cardiovascular and cerebrovascular disease, cancer, diabetes, and chronic respiratory disease, etc.; and cardiovascular and cerebrovascular disease includes hypertension, stroke and coronary heart disease, etc. Data shows that there are more Chinese citizens suffering from chronic disease such as hypertension, diabetes, and dyslipidemia, etc. Data shows that one of the causes of chronic disease is an unhealthy lifestyle. For example, unhealthy lifestyles include irrational diet, insufficient exercise, tobacco use, and excessive alcohol intake, etc. Therefore, with respect to a patient with chronic disease, in addition to medical treatment (e.g., treatment with drugs) based on the patient's disease condition, a doctor also needs to provide the patient with rationalized suggestions on coping with the chronic disease (e.g., dietary suggestion, exercise suggestion, etc.) as auxiliary means for cooperating with medical treatment to better control and prevent the chronic disease. For example, the above-described combination of coping approach suggestions for controlling and preventing chronic disease is referred to as a health prescription.

SUMMARY

An embodiment of the present disclosure provides a health managing method, and the method comprises: connecting to an object information database, and acquiring at least one piece of physical sign data of an object from the object information database, wherein the at least one piece of physical sign data includes an examination result of at least one physical sign examination item in which the object participates; automatically determining at least a health management influencing factor at least based on the at least one piece of physical sign data; and automatically generating a coping approach recommendation form at least based on the health management influencing factor, wherein the coping approach recommendation form is used to generate a coping approach suggestion form.

For example, the health managing method of an embodiment of the present disclosure further comprises: receiving, from a client, basic information data of the object, which is generated according to a basic information filling operation, and questionnaire assessment data of the object, which is generated according to a health questionnaire filling operation; and supplying the basic information data of the object and the questionnaire assessment data of the object to the object information database, wherein the basic information data of the object includes: at least one selected from the group consisting of a current disease history of the object, a family disease history of the object, past disease information of the object, a surgical history of the object, a medication history of the object, an allergy history of the object, and lifestyle information of the object, as well as a gender of the object, a birth date of the object, a height of the object, and a weight of the object.

For example, the health managing method of an embodiment of the present disclosure further comprises: receiving, from the client, a review result, generated according to an information review operation, of at least one item of the basic information data of the object and the questionnaire assessment data of the object; and updating, in response to an omission or error in at least one item of the basic information data of the object and the questionnaire assessment data of the object, at least one item of the basic information data of the object and the questionnaire assessment data of the object in the object information database based on the review result.

For example, the health managing method of an embodiment of the present disclosure further comprises: automatically generating a physical sign examination recommendation item based on at least one selected from the group consisting of the basic information data of the object and the questionnaire assessment data of the object.

For example, the health managing method of an embodiment of the present disclosure further comprises: receiving, from the client, physical sign examination report data of the object, which is generated according to a physical sign examination report uploading operation; and acquiring, from the physical sign examination report data of the object, physical sign data included in the examination result of the physical sign examination item in which the object participates.

For example, in the health managing method of an embodiment of the present disclosure, the physical sign examination report data of the object includes report data of a physical sign examination in which the object participated previously; the physical sign data included in the examination result of the physical sign examination item in which the object participates includes the physical sign data included in the examination result of the physical sign examination item in which the object previously participated; the health managing method further comprises: supplying the physical sign data included in the examination result of the physical sign examination item in which the object previously participated to the object information database; and the automatically generating a physical sign examination recommendation item based on at least one selected from the group consisting of the basic information data of the object and the questionnaire assessment data of the object includes: automatically generating the physical sign examination recommendation item based on at least one selected from the group consisting of the basic information data of the object and based on the questionnaire assessment data of the object and the physical sign data included in the examination result of the physical sign examination item in which the object previously participated.

For example, in the health managing method of an embodiment of the present disclosure, the physical sign examination report data of the object includes data of a physical sign examination report of a physical sign examination item in which the object actually participates among automatically generated physical sign examination recommendation items; the physical sign data included in the examination result of the physical sign examination item in which the object participates includes the physical sign data included in the physical sign examination report of the physical sign examination item in which the object actually participates among the automatically generated physical sign examination recommendation items; and the health managing method further includes: supplying the physical sign data included in the physical sign examination report of the physical sign examination item in which the object actually participates among the automatically generated physical sign examination recommendation items to the object information database.

For example, in the health managing method of an embodiment of the present disclosure, the automatically generating a coping approach recommendation form at least based on the health management influencing factor includes: automatically determining a grade of the object based on the health management influencing factor, and automatically generating the coping approach recommendation form based on at least one selected from the group consisting of the grade of the object and the health management influencing factor; and the coping approach recommendation form includes at least one selected from the group consisting of a recommended drug list, a recommended diet plan list, a recommended exercise plan list, and a recommended management cycle.

For example, the health managing method of an embodiment of the present disclosure further comprises: connecting to the object information database, and acquiring a drug contraindication of the object from the object information database, wherein the health management influencing factor includes a concomitant clinical disease factor; the automatically generating a coping approach recommendation form includes automatically generating the recommended drug list; and the automatically generating the recommended drug list includes: connecting to a drug information database to acquire an available drug list; eliminating inapplicable drugs in the available drug list based on the concomitant clinical disease factor and the drug contraindication of the object, to acquire an applicable drug list; and determining the recommended drug list from the applicable drug list based on the grade of the object.

For example, the health managing method of an embodiment of the present disclosure further comprises: connecting to the object information database, and acquiring a gender of the object, an age of the object, a height of the object, a weight of the object, a diet preference of the object or a dietary taboo of the object from the object information database; and automatically generating the recommended diet plan list at least based on the gender of the object, the age of the object, the height of the object, the weight of the object, the diet preference of the object, the dietary taboo of the object or the health management influencing factor or any combination thereof.

For example, the health managing method of an embodiment of the present disclosure further comprises: connecting to the object information database, and acquiring an exercise preference of the object from the object information database; and automatically generating the recommended exercise list at least based on the grade of the object, the exercise preference of the object and a predetermined exercise principle.

For example, the health managing method of an embodiment of the present disclosure further comprises: connecting to the object information database, and acquiring a gender of the object, an age of the object, a height of the object, a weight of the object, lifestyle information of the object or a family disease history of the object from the object information database, wherein the automatically determining at least the health management influencing factor at least based on the at least one piece of physical sign data includes: automatically determining the health management influencing factor at least based on the gender of the object, the age of the object, the height of the object, the weight of the object, the lifestyle information of the object or the family disease history of the object as well as the at least one piece of physical sign data; and the health management influencing factor include at least one selected from the group consisting of a risk factor of a predetermined disease, target organ injury of a predetermined disease, and a concomitant clinical disease.

For example, in the health managing method of an embodiment of the present disclosure, the automatically determining the grade of the object based on the health management influencing factor includes: determining a temporary grade of the object based on a core factor in the health management influencing factor, and determining the grade of the object based on the temporary grade of the object and other factor than the core factor in the health management influencing factor; and the health management influencing factor include at least one selected from the group consisting of a risk factor of a predetermined disease, target organ injury of a predetermined disease, and a concomitant clinical disease.

For example, the health managing method of an embodiment of the present disclosure further comprises: connecting, in response to that a number of pieces of physical sign data satisfying the predetermined time condition is less than a required number of pieces of physical sign data, to the object information database, and acquiring past disease information of the object from the object information database, wherein the acquiring past disease information of the object from the object information database includes: acquiring at least one piece of physical sign data of the object that satisfies a predetermined time condition from the object information database.

For example, the health managing method of an embodiment of the present disclosure further comprises: receiving, from the client, coping approach recommendation form adjustment data generated according to a coping approach recommendation form adjustment operation; and adjusting the coping approach recommendation form based on the coping approach recommendation form adjustment data, to generate the coping approach suggestion form, wherein the coping approach suggestion form includes at least one selected from the group consisting of a drug regimen, a diet plan, an exercise plan, and a management cycle.

For example, the health managing method of an embodiment of the present disclosure further comprises: receiving, from the client or a physical sign monitoring device used by the object, at least one piece of updated physical sign data of the object that is generated by the physical sign monitoring device used by the object; and outputting, in response to the updated physical sign data being abnormal, a first alarm instruction.

For example, the health managing method of an embodiment of the present disclosure further comprises: receiving, from the client, execution confirmation data generated according to a coping approach suggestion form execution confirmation operation; and outputting, in response to not receiving the execution confirmation data from the client within a predetermined time period, a second alarm instruction.

For example, the health managing method of an embodiment of the present disclosure further comprises: receiving, from the client, the coping approach suggestion form adjustment data generated according to the coping approach suggestion form adjustment operation; updating the coping approach recommendation form based on the coping approach suggestion form adjustment data; receiving, from the client, visit data generated according to a visit status filling operation; and automatically generating a health stage summary at least based on the visit data.

An embodiment of the present disclosure provides a computing device, comprising: one or more processors; one or more storage devices on which computer program instructions are stored, wherein when run by the one or more processors, the computer program instructions execute any one of the above-described health managing methods.

An embodiment of the present disclosure provides a non-transitory storage medium, comprising stored computer program instructions, wherein when run by a processor, the stored computer program instructions execute any one of the above-described health managing methods.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

FIG. 1 is an exemplary flow chart of a health managing method provided by at least one embodiment of the present disclosure;

FIG. 2A is a schematic diagram of a physical sign examination report list uploaded by an object;

FIG. 2B shows a schematic diagram of a result of grading an object by using a health managing method provided by at least one embodiment of the present disclosure;

FIG. 3 is a schematic diagram of a recommended diet plan list automatically generated by using a health managing method provided by at least one embodiment of the present disclosure;

FIG. 4 is a schematic diagram of a recommended exercise plan list automatically generated by using a health managing method provided by at least one embodiment of the present disclosure;

FIG. 11 is a schematic diagram of a health supervision page included in by a medical worker client provided by at least one embodiment of the present disclosure;

FIG. 15 shows a schematic diagram of an entry administration subpage included by a medical worker client provided by at least one embodiment of the present disclosure;

FIG. 17 shows a schematic diagram of an account setting subpage included by a medical worker client provided by at least one embodiment of the present disclosure;

FIG. 19 shows a schematic diagram of an entry administration subpage included by an administrator client provided by at least one embodiment of the present disclosure;

FIG. 20 shows a schematic diagram of a health supervision subpage included by an administrator client provided by at least one embodiment of the present disclosure;

FIG. 22 shows a schematic diagram of a medical worker administration subpage included by an administrator client provided by at least one embodiment of the present disclosure;

FIG. 26 shows still another schematic diagram of a customer administration subpage included by a second administrator client provided by at least one embodiment of the present disclosure;

FIG. 27 shows a schematic diagram of an order administration subpage included by a second administrator client provided by at least one embodiment of the present disclosure;

DETAILED DESCRIPTION

Figure 2C:
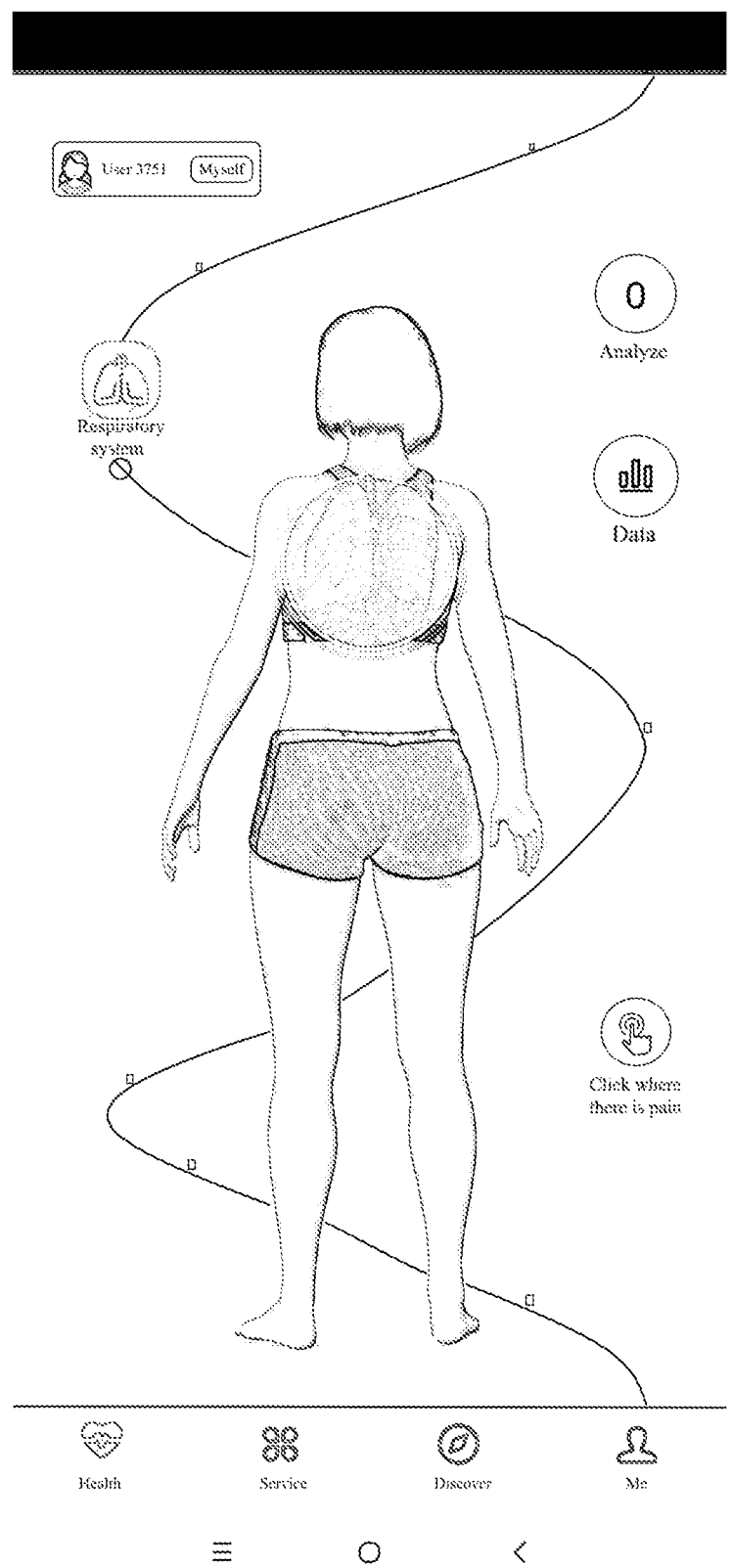
FIG. 2C is a schematic diagram of a digital human body provided by at least one embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, a signal connection, or communication connection, which is conducted directly or indirectly. "On," "under," "right," "left" and the like are only used to indicate relative position relationship, and when the position of the object which is described is changed, the relative position relationship may be changed accordingly.

Optical Character Recognition (OCR) technology: the OCR technology refers to a process that an electronic device (e.g., a scanner or a digital camera) detects characters printed on paper, determines their shapes by detecting dark and light patterns, and then translates the shapes into computer text by using a character recognition method; that is, a technology of optically converting, with respect to printed characters, a text in a paper document into an image file of a black and white dot matrix, and converting the characters in the image into a text format through recognition software for further editing and processing by text processing software.

Natural Language Processing (NLP) technology: it may identify abnormality in an examination report of the object and examination items involved in abnormality, through natural language processing on the object's past examination report data.

At least an inventor of the present disclosure notices in research that, currently, doctors are less efficient in writing health prescriptions for patients (e.g., providing chronic disease coping approach suggestions). This is because the current information system used by the doctors only allows the doctors to manually enter health prescription information for patients currently seeking medical consultation in a text box for entering health prescription contents.

At least an inventor of the present disclosure also notices in research that, pertinence of the current health prescriptions is poor. On the one hand, the current health prescriptions are not intuitive; for example, a health prescription may include contents of "low-oil and low-salt diet" or "total salt within 6 grams per day"; however, even if a patient understands an upper limit for intake of oil and salt in daily diet, the patient may not know the amount of oil and salt included in each meal. On the other hand, a patient with chronic disease usually asks his/her doctor to update a health prescription every six months, and with progression or remission of a disease condition of the patient with chronic disease, pertinence of the health prescription may gradually become worse.

At least an inventor of the present disclosure also notices in research that, at least for reasons below, patients with chronic disease currently have low compliance with health prescriptions. Firstly, health prescriptions are not intuitive, and patients with chronic disease may not know how to execute them, or may not execute them correctly. Secondly, patients with chronic disease cannot intuitively obtain benefits of complying with health prescriptions. In addition, in the absence of external supervision, patients need to have strong perseverance to adhere to health prescriptions for a long time, especially after remission of the disease.

At least one embodiment of the present disclosure provides a health managing method and a storage medium. The health managing method includes: connecting to an object information database, and acquiring at least one piece of physical sign data of an object from the object information database, here, the at least one piece of physical sign data including an examination result of at least one physical sign examination item in which the object participates; automatically determining at least a health management influencing factor at least based on the at least one piece of physical sign data; and automatically generating a coping approach recommendation form at least based on the health management influencing factor. The coping approach recommendation form is used to generate a coping approach suggestion form.

For example, the health managing method can increase a speed of generating the coping approach suggestion form, and thus can improve efficiency of medical workers. For example, the coping approach suggestion form may be referred to as a health prescription. For example, health prescriptions are more often used as an auxiliary means of cooperating with medical treatment.

For example, the health managing method provided by at least one embodiment of the present disclosure may implement a corresponding health managing system or health managing apparatus.

In one example, the health managing method may be implemented based on a server (e.g., a back end); in this case, the coping approach recommendation form and the coping approach suggestion form acquired based on the above-described health managing method may be output by the server (e.g., the back end) and transferred to a client or local end (e.g., a front end) for display on the client or local end (e.g., the front end). For example, the server (e.g., the back end) is further configured to save the coping approach suggestion form acquired based on the above-described health managing method in at least one selected from the group consisting of the server and a memory (e.g., a database associated with the server). For example, the above-described client or local end may be at least one selected from the group consisting of a network end, a mobile end, and a desktop end. For example, the mobile end may be implemented by an APP and an applet. For example, the applet may be a WeChat applet, an Alipay applet, or other applicable applets. For example, the network end may be referred to as a front-end page. For example, during execution of the above-described health managing method, it is necessary to use relevant data acquired via the client or local end.

For example, by making the health managing method be implemented based on the server, and allowing the coping approach recommendation form and the coping approach suggestion form acquired based on the above-described health managing method to be output by the server and transferred to the client or local end, the health managing method can involve more complex operations, for example, the health managing method can automatically generate the coping approach recommendation form based on more factors, which, thus, can improve administration effect of the health managing method. For example, by making the health managing method be implemented based on the server, the health managing method can also involve a plurality of types of users more conveniently, for example, objects, medical workers, medical worker administrators, etc., so that health management effect can be improved with the help of a plurality of types of users.

For example, the client may include an object client and a medical worker client. For example, the object client may be implemented by an APP or an Applet. For example, the medical worker client may be implemented by a network. For example, the medical worker may be at least one selected from the group consisting of a doctor, a nurse, or a health manager.

For example, a medical worker may be a single individual, for example, a medical worker may be a single health manager, that is, at a same time period, only a single health manager formulates a coping approach suggestion form; however, in a case where an object's status is more complicated and the health manager is not sure whether the coping approach recommendation form or the coping approach suggestion form is applicable to the object, the health manager may ask a doctor for help, the doctor may give suggestions, and the health manager may adjust the coping approach recommendation form or the coping approach suggestion form based on the doctor's suggestions.

For example, medical workers may include a plurality of individuals; in one example, a medical worker may be a combination of a health manager and a doctor, that is, the health manager and the doctor jointly formulate a coping approach suggestion form. For example, the health manager may formulate a draft coping approach suggestion form, and the doctor may review the draft coping approach suggestion form to acquire a reviewed coping approach suggestion form. For example, if the draft coping approach suggestion form is not fully applicable to an object, the doctor adjusts the draft coping approach suggestion form. For example, the above-described doctor may be a single doctor, or a combination of a junior doctor and a senior doctor.

It should be noted that, for convenience of description, exemplarily described will be given below by taking that the health managing method provided by at least one embodiment of the present disclosure may be implemented based on a server; however, the health managing method provided by at least one embodiment of the present disclosure is not limited to be implemented based on a server, in some examples, the health managing method provided by at least one embodiment of the present disclosure may also be implemented by a client (or a local end) or by mutual cooperation of the client (or the local end) and the server, and no details will be repeated here.

Hereinafter, non-limiting description of the health managing method provided by the embodiments of the present disclosure will be given through several examples and embodiments; as described below, different features in these specific examples and embodiments may be mutually combined without conflict, to acquire new examples and embodiments, and these new examples and embodiments also belong to the protection scope of the present disclosure.

It should be noted that, for convenience of description, at least one embodiment of the present disclosure describes the health managing method provided by at least one embodiment of the present disclosure by taking that the chronic disease suffered by the object is hypertension; however, at least one embodiment of the present disclosure is not limited thereto; and the health managing method provided by at least one embodiment of the present disclosure is also applicable to managing other chronic disease such as diabetes.

FIG. 1 is an exemplary flow chart of a health managing method provided by at least one embodiment of the present disclosure. As shown in FIG. 1 below, the health managing method includes step S110 to step S130.

Step S110: connecting to an object information database, and acquiring at least one piece of physical sign data of an object from the object information database, here, the at least one piece of physical sign data including an examination result of at least one physical sign examination item in which the object participates;

Step S120: automatically determining at least a health management influencing factor at least based on the at least one piece of physical sign data.

Step S130: automatically generating a coping approach recommendation form at least based on the health management influencing factor. Here, the coping approach recommendation form is used to generate a coping approach suggestion form.

For example, the object is a patient currently seeking medical consultation (e.g., a patient with chronic disease). For example, the at least one piece of physical sign data includes an examination result of at least one physical sign examination item in which the object participates. For example, physical sign data may also be referred to as medical data. For example, the examination result of at least one physical sign examination item is an electronic examination result; and correspondingly, the at least one physical sign data is electronic data.

For example, the physical sign examination item include physical sign examination items for the chronic disease that the object is currently seeking medical consultation for, and physical sign examination items for other related disease (e.g., chronic kidney disease) that the object may have. For example, physical sign examination items include but are not limited to "blood pressure (systolic blood pressure and/or diastolic blood pressure) examination items", "pulse examination items", "body temperature examination items", "heart rate examination items", "blood glucose examination (e.g., at least one selected from the group consisting of fasting blood glucose test, 2-hour postprandial blood glucose test, glycosylated hemoglobin test) items", "blood lipid examination (e.g., at least one high-density lipoprotein-cholesterol test, triglyceride test, low-density lipoprotein-cholesterol test, and total cholesterol test) items", "white blood cell count test items", "average platelet volume test items", "Body Mass Index (BMI) examination items", "waist circumference examination items", "abdominal B-ultrasound examination items", "cardiac B-ultrasound examination items", and "X-ray examination items".

For example, the at least one physical sign examination item involves an indicator of whether the patient currently seeking medical consultation has at least one selected from the group consisting of a variety of disease (e.g., chronic disease). For example, the "systolic blood pressure examination item" involves an indicator of whether the patient currently seeking medical consultation has hypertension.

For example, the physical sign data includes at least one selected from the group consisting of blood pressure data (systolic blood pressure data and/or diastolic blood pressure data), pulse data, body temperature data, heart rate data, blood glucose data (e.g., at least one selected from the group consisting of fasting blood glucose data, 2-hour postprandial blood glucose data, glycosylated hemoglobin data), blood lipid data (e.g., at least one high-density lipoprotein-cholesterol data, triglyceride data, low-density lipoprotein-cholesterol data, and total cholesterol data), white blood cell count data, average platelet volume data, Body Mass Index (BMI), waist circumference, data corresponding to abdominal B-ultrasound images, data corresponding to cardiac B-ultrasound images, and data corresponding to X-ray images. For example, "abdominal B-ultrasound examination items" and "cardiac B-ultrasound examination items", can not only provide ultrasound images, but also provide key data the ultrasound images involve. For example, abdominal B-ultrasound examination result include description "a 1.1 cm×1.2 cm×1.7 cm hypoechoic region visible in the liver". For example, an image processing technology may be used to extract required data from medical images such as ultrasound images and X-ray images. For example, the image processing technology may be used to extract sizes of lung nodules in X-ray images.

For example, the health managing method further includes acquiring the information data of the object, and supplying the information data of the object to the object information database, to construct the object information database. For example, the information data of the object may be acquired and the object information database may be constructed based on at least part of step S141 to step S148.

For example, the health managing method further includes step S141 and step S142.

Step S141: receiving, from a client (e.g., an object client), the basic information data of the object, which is generated according to a basic information filling operation, and the questionnaire assessment data of the object, which is generated according to a health questionnaire filling operation.

For example, the basic information data of the object includes: at least one (e.g., all) selected from the group consisting of a current disease history of the object, a family disease history of the object, past disease information of the object, a surgical history of the object, a medication history of the object, an allergy history of the object, and lifestyle information of the object, as well as a gender of the object, a birth date of the object, a height of the object, and a weight of the object. For example, lifestyle information of the object includes the smoking history or the passive smoking history of the object.

In some examples, the basic information data of the object may include parts of a gender of the object, a birth date of the object, a height of the object, and a weight of the object. For example, the basic information data of the object may include the object's other information data. For example, the basic information data of the object may include the age of the object but not the birth date of the object.

For example, the questionnaire assessment data of the object includes at least one of the object's physical disease assessment data, the object's lifestyle assessment data, the object's mental and psychological assessment data, and the object's disease history screening assessment data, or any combination thereof.

For example, by receiving, from the client (e.g., the object client), the questionnaire assessment data of the object generated according to the health questionnaire filling operation, more information about the object may be acquired, thereby making the automatically generated coping approach recommendation form more applicable.

For example, in a registration link before using the client (e.g., the object client) for a first time, the object may input the basic information data of the object in the client (e.g., the object client), then fill in the health questionnaire in the client (e.g., the object client) after registration is completed, so the client (e.g., the object client) may acquire the basic information data of the object generated according to the basic information filling operation and the questionnaire assessment data of the object generated according to the health questionnaire filling operation, and supply the basic information data of the object generated according to the basic information filling operation and the questionnaire assessment data of the object generated according to the health questionnaire filling operation to the server.

It should be noted that, the health managing method provided by at least one embodiment of the present disclosure is not limited to receiving, from the client (e.g., the object client), the basic information data of the object generated according to the basic information filling operation and the questionnaire assessment data of the object generated according to the health questionnaire filling operation. In some examples (e.g., with respect to an example in which the object does not execute the health questionnaire filling operation), the health managing method provided by at least one embodiment of the present disclosure may also not receive, from the client (e.g., the object client), the questionnaire assessment data of the object generated according to the health questionnaire filling operation. In other examples, the basic information filling operation and the health questionnaire filling operation may be combined as the health questionnaire filling operation.

Step S142: supplying the basic information data of the object and the questionnaire assessment data of the object to the object information database.

For example, by supplying the basic information data of the object and the questionnaire assessment data of the object to the object information database, the object information database may be constructed, so that related information of the object may be acquired more conveniently when executing the health managing method (e.g., automatically generating the coping approach recommendation form).

For example, the health managing method further includes step S143.

Step S143: automatically generating a physical sign examination recommendation item based on at least one selected from the group consisting of the basic information data of the object and the questionnaire assessment data of the object.

For example, the physical sign examination recommendation item includes physical sign examination items for the chronic disease (e.g., hypertension) that the object is currently seeking medical consultation for, and a physical sign examination item for other related diseases that the object may have.

For example, in a case where the chronic disease that the object is currently seeking medical consultation for is hypertension, the physical sign examination item for the chronic disease that the object is currently seeking medical consultation for include: height, weight, abdominal circumference, systolic blood pressure, and diastolic blood pressure.

For example, because hypertension may injure heart, brain, kidneys, eyes, blood vessels and other organs, and cause some complications, the physical sign examination item for other related diseases that the object may have may include cardiac color Doppler ultrasound (e.g., ultrasound cardiogram), cervical vascular color Doppler ultrasound (e.g., carotid artery ultrasound), renal function, fundus detection (e.g., ophthalmoscope), electrocardiogram, and other examinations.

For example, in a case where the object also suffers from diabetes and hyperlipidemia, the physical sign examination item for other related diseases that the object may have may include blood glucose test (e.g., oral glucose tolerance test) and blood lipid test.

For example, by automatically generating the physical sign examination recommendation item, the object may participate in the physical sign examination recommendation item in advance before communicating with a medical worker; in this case, the medical worker already acquires examination result of the physical sign examination item in which the object participated before the object communicates with the medical worker, which, thus, can reduce frequency of communication between the object and the medical worker without reducing a communication effect, and can further save time for the object, for example, may avoid that the object waits a long time in order to acquire the physical sign examination recommendation item.

For example, by automatically generating the physical sign examination recommendation item based on the basic information data of the object and the questionnaire assessment data of the object, the physical sign examination recommendation item may be more matched with the patient's personal status (e.g., to avoid omitting important physical examinations). For example, based on the object's lifestyle assessment data, it is possible to determine disease that the object's lifestyle may cause, and to confirm whether the object has the above-described possible disease through physical sign examinations, which, thus, can avoid omitting physical examinations for the above-described possible disease.

For example, the object may participate in the physical sign examination recommendation item in advance before communicating with the medical worker; in this case, before the object communicates with the medical worker, the medical worker already obtains examination result of the physical sign examination item in which the object participated, which, thus, can reduce frequency of communication between the object and the medical worker without reducing a communication effect, and further save time for the object, for example, avoid that the object waits a long time in order to acquire a recommended physical sign examination item list (e.g., avoid waiting for a doctor to prescribe a physical examination sheet).

For example, the object may participate in at least part of the physical sign examination recommendation item automatically generated according to his/her own status. For example, the automatically generating the physical sign examination recommendation item includes that: in a case where there are both physical sign examination items in which the object has participated within a predetermined time limit and physical sign examination items in which object has not participated within the predetermined time limit, the object may only participate in the physical sign examination item in which he/she has not participated within the predetermined time limit, which, thus, can save time for the object and reduce costs of physical examination.

For example, the physical sign examination item in which the object has participated within the predetermined time limit refers to physical sign examination items in which the object has participated within the predetermined time limit before automatically generating the physical sign examination recommendation item (e.g., within three months before automatically generating the physical sign examination recommendation item).

For example, the health managing method further includes acquiring physical sign data included in examination result of the physical sign examination item in which the object previously participated to automatically generate the physical sign examination recommendation item; in this case, the automatically generating a physical sign examination recommendation item based on at least one selected from the group consisting of the basic information data of the object and the questionnaire assessment data of the object includes: automatically generating the physical sign examination recommendation item based on at least one (e.g., all) of the basic information data of the object and the questionnaire assessment data of the object and the physical sign data included in the examination result of the physical sign examination item in which the object previously participated. For example, by automatically generating the physical sign examination recommendation item based on at least one selected from the group consisting of the basic information data of the object and based on the questionnaire assessment data of the object and the physical sign data included in the examination result of the physical sign examination item in which the object previously participated, it can be avoided that the physical sign examination recommendation item includes the physical sign examination item in which the object has already participated within the predetermined time limit, that is, more suitable physical sign examination items are recommended based on the examination result of the physical sign examination item participated in previously.

For example, the health managing method further includes step S144.

Step S144: receiving, from the client (e.g., the object client), the physical sign examination report data of the object, which is generated according to a physical sign examination report uploading operation.

For example, in step S144, the object may upload a physical sign examination report via the client (e.g., the object client), so the client (e.g., the object client) may acquire the physical sign examination report data of the object, which is generated according to the physical sign examination report uploading operation, and supply the physical sign examination report data of the object, which is generated according to the physical sign examination report uploading operation to the server.

For example, the physical sign examination report uploaded by the object via the client (e.g., the object client)

may be an image or a document (e.g., PDF). FIG. 2A is a schematic diagram of a physical sign examination report list uploaded by an object.

Step S145: acquiring, from the physical sign examination report data of the object, physical sign data included in the examination result of the physical sign examination item in which the object participates.

For example, the physical sign data included in the examination result of the physical sign examination item in which the object participates acquired from the physical sign examination report data of the object may be structured data, which, thus, is favorable for retrieval and display in a graphical user interface. For example, structured data is relational model data, which may be stored in a relational database. For example, unstructured data is data that has no fixed pattern and may be stored in a non-relational database. For example, structured data may be understood by a computer, so it is favorable for retrieval and display on a graphical user interface. For example, "platelet count"-"value"-"215" is a kind of structured data; for example, "platelet packed volume"-"value"-"0.2" is also a kind of structured data.

In one example, the physical sign examination report data of the object includes data of the physical sign examination report of the object. For example, the data of the physical sign examination report of the object includes a page of the physical sign examination report; in this case, verified character information of an image of the page may be acquired by executing an applicable image character information acquiring method, and the verified character information of the image of the page is structured, to acquire structured data. For example, the data of the physical sign examination report may be data in image format (JPEG format) or document (e.g., DOCX or PDF) format. For example, the object may acquire a physical sign examination report in image format by taking a photo or scanning a paper physical sign examination report. For example, the object may acquire a physical sign examination report in PDF format by scanning a paper physical sign examination report. For example, the object may acquire a physical sign examination report in DOCX format from information platforms of a medical institution and a physical examination institution. For example, the image or document corresponding to the data of the physical sign examination report contains a chart; and the data of the physical sign examination report may also be referred to as chart data.

For example, the image character information acquiring method includes: acquiring an image (e.g., an image of a page of a physical sign examination report, and data of the physical sign examination report in image format) and extracting at least one item of character information included in the image; and verifying the at least one item of character information based on a knowledge map (e.g., a medical examination knowledge map). For example, by verifying the extracted at least one item of character information based on the knowledge map, accuracy of the acquired character information can be improved. For example, an optical character recognition technology may be used to extract the at least one item of character information included in the image.

For example, the verifying at least one item of character information based on a knowledge map includes: confirming character information with errors in the at least one item of character information based on the knowledge map; and correcting the character information with errors based on the knowledge map.

In another example, the physical sign examination report data of the object includes document data of the physical sign examination report of the object. For example, the character information is extracted from the document data of the physical sign examination report of the object, and the character information is structured to obtain structured data.

For example, the physical sign examination report data of the object includes at least one category of report data of a physical sign examination in which the object participated previously and data of physical sign examination reports of physical sign examination items in which the object actually participates among the automatically generated physical sign examination recommendation items.

For example, the physical sign data included in the examination result of the physical sign examination item in which the object participates includes: at least one category of the physical sign data included in the examination result of the physical sign examination item in which the object previously participated, and the physical sign data included in the physical sign examination report of the physical sign examination item in which the object actually participates among the automatically generated physical sign examination recommendation items.

For example, the health managing method further includes step S146.

Step S146: supplying the physical sign data included in the examination result of the physical sign examination item in which the object previously participated, and the physical sign data included in the physical sign examination report of the physical sign examination item in which the object actually participates among the automatically generated physical sign examination recommendation items to at least one selected from the group consisting of the object information databases.

It should be noted that, the health managing method provided by at least one embodiment of the present disclosure is not limited to acquiring the physical sign data included in the examination result of the physical sign examination item in which the object participates from the physical sign examination report data of the object, which is generated according to the physical sign examination report uploading operation.

For example, the health managing method provided by at least one embodiment of the present disclosure may further include acquiring at least one piece of physical sign data of the object from a physical sign examination item result data source, and supplying the at least one piece of physical sign data of the object acquired from the physical sign examination item result data source to the object information database. For example, the at least one category of the physical sign data included in the examination result of the physical sign examination item in which the object previously participated, and the physical sign data included in the physical sign examination report of the physical sign examination item in which the object actually participates among the automatically generated physical sign examination recommendation items may be acquired from the physical sign examination item result data source.

For example, the physical sign examination item result data source includes at least one selected from the group consisting of information administrating systems (e.g., laboratory information administrating systems) of a health record platform and a medical institution (e.g., a hospital or a physical examination institution). For example, the health record platform may dock with at least one (e.g., a plurality of) medical institutions, and acquire, from the at least one (e.g., the plurality of) medical institutions, examination result of patients who participated in physical sign examinations at these medical institutions. For example, the health record platform may also acquire, from smart terminals (e.g., bracelets, smart watches, smart body fat scales, blood pressure meters, smart glasses, smart shoes, smart hats, smart clothes, etc.), at least one piece of physical sign data (e.g., pulse, body temperature, heart rate, respiration, brain electricity, electrocardiogram, blood pressure, blood oxygen, myoelectricity, etc.) of patients detected by sensors in the smart terminals. For example, the health record platform may periodically (e.g., daily) acquire, from a plurality of medical institutions, examination result of patients who participated in physical sign examinations at these medical institutions, and pre-store the same in a database (or a memory) associated with the health record platform. For example, when a patient participates in a physical sign examination at a medical institution, examination result are uploaded (automatically uploaded) to an information administrating system of the medical institution. For example, at least one piece of physical sign data of the object may be acquired from at least one selected from the group consisting of third-party information administrating systems (e.g., laboratory information administrating systems) such as a health record platform or a medical institution (e.g., a hospital or a physical examination institution), based on a serial number of the object (e.g., a chronic disease number or a medical card serial number of a patient currently seeking medical consultation).

For example, the object may upload the previous physical sign examination report from the client (e.g., the object client), and thus the server may acquire, from the previous physical sign examination report, the physical sign data included in previous physical sign examination report of the object based on step S145; in addition, the server may acquire, directly from a physical examination institution or a hospital, the physical sign data included in the physical sign examination report of the physical sign examination item in which the object actually participates among the automatically generated physical sign examination recommendation items. Hereinafter, exemplary description will be given in conjunction with an example.

In some examples, after the object (e.g., the patient) enters a hypertension management process, he/she fills out a disease history collection questionnaire; thereafter, a health managing system (e.g., a chronic disease managing system) automatically recommends personalized physical examination items; after the object (e.g., the patient) goes to a hospital or a physical examination institution and completes physical examinations, physical examination data is automatically transmitted to the server, for example, an object (e.g., patient) back end; in addition, the object (e.g., the patient) may upload a previous physical examination report on an object client (e.g., an APP end); the health managing system according to the health managing method provided by at least one embodiment of the present disclosure may intelligently recognize the physical examination report and extract a same physical examination item from the previous physical examination report for comparison in terms of time, which can not only facilitate a doctor to understand past disease history of the object (e.g., the patient), but also allow the doctor to view a change (e.g., a trend change) of a predetermined disease of the object (e.g., the patient). For example, the health managing system according to the health managing method provided by at least one embodiment of the present disclosure may recognize physical examination reports (e.g., physical examination reports of PDF version or in image format) originating from different medical institutions that are automatically uploaded by objects (e.g., patients, users), and may view the recognized structured data according to examination items. For example, blood routine items of several physical examination reports may be compared horizontally. For example, the OCR technology may be used to extract character information from a physical examination report in image format, and then verify the extracted characters.

For example, the health managing method further includes at least one selected from the group consisting of step S147 and step S148.

Step S147: receiving, from the client (e.g., a medical worker client), a review result, generated according to an information review operation, of at least one item (e.g., all items) of the basic information data of the object and the questionnaire assessment data of the object.

For example, in step S147, after the object fills in the basic information data of the object and the questionnaire assessment data of the object via the client (e.g., the object client) (e.g., after the object participates in at least a part of the automatically generated physical sign examination recommendation items), the medical worker may make a first visit (e.g., a telephone visit) to the object. For example, during or after the first visit, the medical worker may review at least one item of the basic information data filled by the object and questionnaire assessment data of the object via the client (e.g., the object client); in a case where there is an omission or error in at least one item of the basic information data of the object and the questionnaire assessment data of the object, execute an information review operation via the client (e.g., the medical worker client), so the client (e.g., the medical worker client) may acquire results of reviewing the at least one item of the basic information data of the object and the questionnaire assessment data of the object; and supply the results of reviewing the at least one item of the basic information data of the object and the questionnaire assessment data of the object generated according to the information review operation to the server.

For example, the information review operation includes modifying, deleting or adding at least a part of the basic information data of the object and the questionnaire assessment data of the object. For example, during the first visit, the medical worker may notice that at least one item of the basic information data of the object and the questionnaire assessment data of the object is inconsistent with the results of the physical examination items in which the object actually participates among the automatically generated physical sign examination recommendation items, the medical worker may inquire the object as to whether there is an error in the at least one selected from the group consisting of the basic information data he/she fills in and the questionnaire assessment data of the object; in a case where it is confirmed that there is an error in the at least one item of the basic information data of the object and the questionnaire assessment data of the object, execute the information review operation, that is, modifying, deleting, or adding the part of the basic information data of the object and the questionnaire assessment data of the object that has an omission or error.

Exemplary description will be given below in conjunction with FIG. 2B. FIG. 2B shows a schematic diagram of an object grading result (e.g., cardiovascular grade stratification) acquired by using the health managing method provided by at least one embodiment of the present disclosure. As shown in FIG. 2B, when the medical worker notices that there is an omission of risk factors of a predetermined disease, he/she may execute a review operation by checking omitted risk factors in the graphical user interface shown in FIG. 2B.

Step S148: updating, in response to an omission or error in at least one item of the basic information data of the object and the questionnaire assessment data of the object, at least one item of the basic information data of the object and the questionnaire assessment data of the object in the object information database based on the review result.

For example, in step S148, by updating, in response to an omission or error in at least one item of the basic information data of the object and the questionnaire assessment data of the object, at least one item of the basic information data of the object and the questionnaire assessment data of the object in the object information database based on a review result, the basic information data of the object and the questionnaire assessment data of the object in the object information database may be more reliable, thereby making the automatically generated coping approach recommendation form better match with the personal status of the object.

For example, the health managing method further includes step S149.

Step S149: automatically generating a three-dimensional health record of the object at least based on the basic information data of the object and the questionnaire assessment data of the object. For example, through the three-dimensional health record, a three-dimensional human body model may be used to visually display the object's physical abnormalities, comprehensive scores, and disease details, etc., so that the object may intuitively understand his/her own status.

For example, the three-dimensional health record of the object may be generated in combination with a digital human body shown in FIG. 2C. For example, by generating the three-dimensional health record of the object with the digital human body, abnormalities of the object (the patient) may be intuitively presented, which is convenient for the doctor to give a pertinent disease condition introduction to the object.

For example, in step S149: the automatically generating a three-dimensional health record of the object at least based on the basic information data of the object and the questionnaire assessment data of the object includes: automatically generating the three-dimensional health record of the object based on the basic information data of the object, the questionnaire assessment data of the object, and the physical sign data included in the examination result of the physical sign examination item in which the object previously participated; and in this case, the three-dimensional health record of the object can be better matched with the personal status of the object.

For example, the health managing method further includes step S1491.

Step S1491: connecting, in response to appointment data generated according to a physical sign examination appointment operation, to a physical sign examination appointment system, and appointing, for the object, based on the appointment data, physical sign examination items to be performed in a time period specified by the object.

For example, the object may browse appointable time for a relevant physical sign examination item from the client (e.g., the object client), and appoint the physical sign examination item for the specified time period via the client (e.g., the object client), so the client (e.g., the object client) may acquire the appointment data generated according to the physical sign examination appointment operation, and supplying the appointment data generated according to the physical sign examination appointment operation to the server.

Figure 2D:
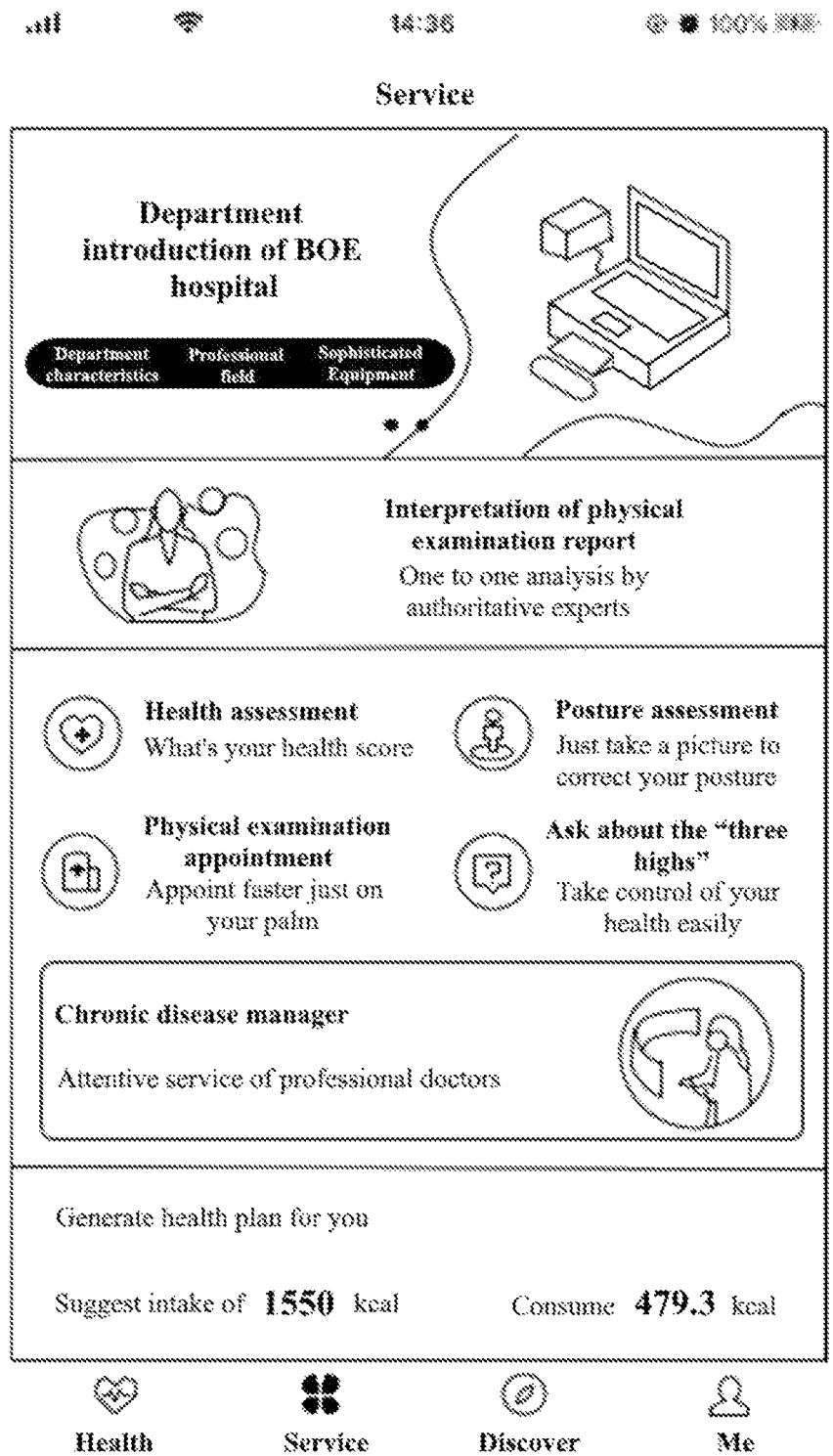
FIG. 2D is a schematic diagram of a physical examination appointment entrance of an object client provided by at least one embodiment of the present disclosure.

FIG. 2D is a schematic diagram of a physical examination appointment entrance of an object client provided by at least one embodiment of the present disclosure. For example, the object may enter a physical examination appointment subpage of the object client through the physical examination appointment entrance of the object client shown in FIG. 2D, and execute a physical sign examination appointment operation on the physical examination appointment subpage of the object client.

For example, the health managing method further includes step S1492.

Step S1492: outputting, in response to the appointment data generated according to the physical sign examination appointment operation, pre-examination precautions of the physical sign examination item appointed by the object.

For example, the pre-examination precautions of the physical sign examination item appointed by the object may be output by the server to the client (e.g., the object client), and displayed on the graphical user interface of the client (e.g., the object client). For example, when the object makes an appointment for a blood glucose test (e.g., an oral glucose tolerance test), pre-examination precautions include that: the test should be performed on an empty stomach in early morning after 8 to 12 hours of fasting.

For example, by outputting, in response to the appointment data generated according to the physical sign examination appointment operation, the pre-examination precautions of the physical sign examination item appointed by the object, the object may be prevented from violating the pre-examination precautions so that the object cannot perform the physical sign examination item at the specified time.

For example, the health managing method further includes step S1493.

Step S1493: connecting, in response to the appointment data generated according to the physical sign examination appointment operation, to a payment system.

For example, the health managing method further includes step S1494.

Step S1494: connecting, in response to an operation based on clicking a "pre-examination inquiry button", the client (e.g., the object client) to an inquiry platform.

For example, by connecting, in response to the operation based on clicking the "pre-examination inquiry button", the client (e.g., the object client) to the inquiry platform, the object may better understand whether he/she needs to participate in a specified physical examination item or better understand whether the pre-examination precautions are violated.

For example, step S141 to step S149 and step S1491 to step S1494 may be executed before step S110 to step S130 are executed.

For example, the object information database may be constructed based on step S141 to step S148. For example, step S141 to step S143 and step S1491 to step S1494 may be executed before the object participates in the automatically generated physical sign examination recommendation items.

For example, step S149 may be executed before the object participates in the automatically generated physical sign examination recommendation items. For another example, step S149 may be executed after step S141 to step S143, and before step S1491 to step S1494.

For example, step S144 to step S146 may be executed before the object participates in the automatically generated physical sign examination recommendation items; for another example, step S144 to step S146 may be executed after the object participates in the automatically generated physical sign examination recommendation items; for another example, step S144 to step S146 may be executed before and after the object participates in the automatically generated physical sign examination recommendation items.

In some examples, step S147 and step S148 may be executed before the object participates in the automatically generated physical sign examination recommendation items. For example, step S147 and step S148 may be executed after the object participates in at least part of the automatically generated physical sign examination recommendation items, in this case, the medical worker may review at least one selected from the group consisting of the basic information data of the object and the questionnaire assessment data of the object filled by the object via the client (e.g., the object client) in combination with the results of the physical examination items in which the object actually participated among the automatically generated physical sign examination recommendation items, so medical worker may better discover an omission or error in at least one selected from the group consisting of the basic information data of the object and the questionnaire assessment data of the object.

It should be noted that, step S147 and step S148 are not limited to be executed before the object participates in the automatically generated physical sign examination recommendation items. For example, if the object already participated in the automatically generated physical sign examination recommendation items within the predetermined time period before automatically generating the physical sign examination recommendation item, step S147 and step S148 may be directly executed without waiting for the object to participate in the automatically generated recommended physical sign examination item.

For example, when executing step S120, the health managing method further includes step S151.

Step S151: connecting to the object information database, and acquiring a gender of the object, an age of the object, a height of the object, a weight of the object, lifestyle information of the object or a family disease history of the object from the object information database.

For example, in step S120, the automatically determining at least the health management influencing factor at least based on the at least one piece of physical sign data includes step S121.

Step S121: automatically determining the health management influencing factor at least based on a gender of the object, an age of the object, a height of the object, a weight of the object, lifestyle information of the object or a family disease history of the object as well as at least one piece of physical sign data.

For example, the health management influencing factor include at least one (e.g., all) selected from the group consisting of risk factors of predetermined disease (e.g., a predetermined chronic disease), target organ injuries of predetermined disease, and concomitant clinical disease. For example, the at least one selected from the group consisting of a risk factor of a predetermined disease, target organ injury of a predetermined disease, and a concomitant clinical disease included in the health management influencing factor may be formulated according to medical guidelines for the predetermined disease currently adopted by the medical community. For example, with respect to hypertension, Guidelines for Prevention and Treatment of Hypertension may be used to set at least one selected from the group consisting of risk factors of the predetermined disease, target organ injuries of the predetermined disease, and concomitant clinical disease included in the health management influencing factor.

For example, by formulating at least one selected from the group consisting of a risk factor of a predetermined disease, target organ injury of a predetermined disease, and a concomitant clinical disease included in the health management influencing factor according to the medical guidelines for the predetermined disease currently adopted by the medical community, and automatically generating the coping approach recommendation form at least based on the health management influencing factor, the automatically generated coping approach recommendation form may be made more in line with current medical practice, which, thus, can reduce workload of medical workers to adjust the coping approach recommendation form, and further improve work efficiency of the medical workers.

For example, with respect to hypertension, risk factors of the predetermined disease include: grades of blood pressure (e.g., abnormal blood pressure or high blood pressure); men being over 55 years old and women being over 65 years old; smoking history or passive smoking history; history of diabetes (e.g., glucose tolerance impaired); dyslipidemia (e.g., total cholesterol being about 5.7 mmol/L); family history of early-onset cardiovascular disease (e.g., onset age of a first-degree relative being less than 50 years; obesity, for example, men's waist circumference being greater than or equal to 90 cm, and women's waist circumference being greater than or equal to 85 cm, or BMI being greater than or equal to 28 kg/m$^2$. For example, with respect to hypertension, the target organ injuries of the predetermined disease includes left ventricular hypertrophy, microalbuminuria, etc. For example, with respect to hypertension, the concomitant clinical disease includes cerebrovascular disease, heart disease, kidney disease, diabetes, etc.

For example, step S121 includes step S122 and step S123.

Step S122: automatically determining risk factors of predetermined disease at least based on a gender of the object, an age of the object, a height of the object, a weight of the object, lifestyle information of the object or a family disease history of the object. For example, step S122 includes automatically determining risk factors of predetermined disease based on a gender of the object, an age of the object, a height of the object, a weight of the object, the object's waist circumference, lifestyle information of the object (e.g. the object's smoking or passive smoking history), and a family disease history of the object (e g, family history of early-onset cardiovascular disease).

Step S123: automatically determining at least one (e.g., all) of target organ injuries of predetermined disease and concomitant clinical disease based on at least one piece of physical sign data of the object.

In some examples, step S123 includes: automatically determining at least one selected from the group consisting of target organ injuries of predetermined disease and concomitant clinical disease based on at least one piece of physical sign data of the object and predetermined medical rules.

For example, the at least one piece of physical sign data of the object includes the object's fasting blood glucose; and the predetermined medical rule is to determine that the object has diabetes (e.g., concomitant diabetes) when fasting blood glucose is greater than or equal to 7.0 mmol/L. For example, the predetermined medical rules may be formulated based on medical guidelines for predetermined disease.

For example, step S123 includes automatically determining at least one selected from the group consisting of target organ injuries of predetermined disease and concomitant clinical disease based on at least one piece of physical sign data of the object, the predetermined medical rules, and past disease information of the object.

In one example, when automatically determining at least one selected from the group consisting of target organ injuries of predetermined disease and concomitant clinical disease, physical sign data of the object that satisfies a predetermined time condition may be selected firstly; past disease information provided by the object (e.g., via the object client) is selected secondly; and physical sign data of the object that does not satisfy the predetermined time condition is selected thirdly. For example, past disease information of the object includes information on target organ injuries of the predetermined disease and concomitant clinical disease the object has known. In this case, in step S110, the acquiring at least one piece of physical sign data of an object from the object information database includes: acquiring at least one piece of physical sign data of the object that satisfies a predetermined time condition from the object information database; the health managing method further includes: connecting, in response to that the number of pieces of physical sign data satisfying the predetermined time condition is less than the required number of pieces of physical sign data, to the object information database, and acquiring past disease information of the object from the object information database. For example, when determining whether the object has concomitant clinical disease (e.g., cerebrovascular disease, heart disease, kidney disease, diabetes), physical sign data for determining whether the object has cerebrovascular disease, physical sign data for determining whether the object has heart disease, physical sign data for determining whether the object has kidney disease, and physical sign data for determining whether the object has diabetes are needed; if the physical sign data of the object that satisfies the predetermined time condition only includes the physical sign data for determining whether the object has diabetes, then past disease information of the object may be acquired from the object information database, to determine whether the object has cerebrovascular disease, heart disease or kidney disease.

In another example, when automatically determining at least one selected from the group consisting of target organ injuries of predetermined disease and concomitant clinical disease, the physical sign data of the object (that satisfies or does not satisfy the predetermined time condition) may be selected firstly; and the past disease information provided by the object (e.g., via the object client) is selected secondly.

For example, in step S130, the coping approach recommendation form includes: at least one selected from the group consisting of a recommended drug list, a recommended diet plan list, a recommended exercise plan list, and a recommended management cycle.

For example, in step S130, the coping approach recommendation form may include: a recommended drug list, a recommended diet plan list, and a recommended exercise plan list. For example, in step S130, the coping approach recommendation form may further include a management goal.

For example, in step S130, the automatically generating a coping approach recommendation form at least based on the health management influencing factor includes: automatically determining the grade of the object based on the health management influencing factor, and automatically generating the coping approach recommendation form based on at least one selected from the group consisting of the grade of the object and the health management influencing factor.

For example, the grade of the object may refer to severity of predetermined disease the object has. For example, the grade of the object may be the object's disease risk grade.

For example, in step S130, the automatically determining the grade of the object based on the health management influencing factor includes step S131 and step S132.

Step S131: determining the temporary grade of the object based on a core factor in the health management influencing factor.

For example, in the case where the predetermined disease is hypertension, the core factor in the health management influencing factor is a grade of blood pressure (e.g., abnormal blood pressure or high blood pressure). For example, according to values of blood pressure and Table 1 below, blood pressure may be divided into six categories below, namely, normal blood pressure, high-normal blood pressure, mild hypertension, moderate hypertension, severe hypertension, and isolated systolic hypertension; among the above six categories of blood pressure, temporary grades of objects with mild hypertension, moderate hypertension, and severe hypertension are respectively determined as grade 1, grade 2, and grade 3. In some examples, objects' temporary grade corresponding to a part of a numerical range of normal-high blood pressure (systolic blood pressure of 130 to 139, and diastolic blood pressure of 85 to 89) is determined as grade 0.

It should be noted that, the temporary grade here is a concept in order to automatically determine a grade of an object by using, for example, a computer program, instead of a medical concept; however, the temporary grade here may have a corresponding relationship with the medical concept. For example, in the case where the predetermined disease is hypertension, the temporary grade is not equal to the grade of hypertension, however, grade 1, grade 2, and grade 3 in the temporary grade may respectively correspond to grade-1 hypertension, grade-2 hypertension and grade-3 hypertension; and grade 0 in the temporary grade may correspond to a part of a blood pressure numerical range corresponding to normal-high blood pressure.

TABLE 1

| Blood pressure grade | Systolic blood pressure (mmHg) | Diastolic blood pressure (mmHg) | Temporary grade |
|---|---|---|---|
| Normal blood pressure | <120 | <80 | — |
| High-normal blood pressure | 120-129 | 80-84 | — |
| High-normal blood pressure | 130-139 | 85-89 | Grade 0 |
| Mild hypertension | 140-159 | 90-99 | Grade 1 |
| Moderate hypertension | 160-179 | 100-109 | Grade 2 |
| Severe hypertension | ≥180 | ≥110 | Grade 3 |
| Isolated systolic hypertension | ≥140 | <90 | — |

For example, in a case where systolic blood pressure and diastolic blood pressure of the object correspond to different blood pressure grades, a higher grade of the two blood pressure grades is taken as the blood pressure grade of the object.

For example, with respect to a value source of systolic blood pressure and diastolic blood pressure, values of systolic blood pressure and diastolic blood pressure included in the examination result of the physical sign examination recommendation item in which the object participates are selected firstly; and values of systolic blood pressure and diastolic blood pressure included in the examination result of the physical sign examination item in which the object previously participated are selected secondly. For example, the physical sign examination item in which the object previously participated refer to the physical sign examination item in which the object participated before acquiring the physical sign examination recommendation item.

Step S132: determining the grade of the object based on the temporary grade of the object and other factor than the core factor in the health management influencing factor.

For example, in the case where the predetermined disease is hypertension, other factor than the core factor in the health management influencing factor include: other risk factors of the predetermined disease (e.g., the predetermined chronic disease), a target organ injuries factor of the predetermined disease, and a concomitant clinical disease factor except the core factor in the health management influencing factor.

For example, in step S132, the determining the grade of the object based on the temporary grade of the object and other factor than the core factor in the health management influencing factor includes determining the grade of the object based on the temporary grade of the object, the predetermined medical rules, and other factor than the core factor in the health management influencing factor.

TABLE 2

| | Temporary grade | | | |
| --- | --- | --- | --- | --- |
| Other factors | Grade 0 | Grade 1 | Grade 2 | Grade 3 |
| None | — | Low risk | Medium risk | High risk |
| Including 1-2 other risk factors | Low risk | Medium risk | Medium/ high risk | Very high risk |
| Including 3 or more other risk factors, presence of target organ injuries, or presence of CKD stage 3, and presence of uncomplicated diabetes | Medium/ high risk | High risk | High risk | Very high risk |
| Presence of clinical complications, or presence of CKD stage 4 and above, and presence of complicated diabetes | High/very high risk | Very high risk | Very high risk | Very high risk |

For example, in step S132, the predetermined medical rules are shown in Table 2. In Table 2, CKD is chronic kidney disease, SBP is systolic blood pressure, and DBP is diastolic blood pressure.

For example, with respect to an object satisfying conditions below: male, 56 years old, having smoking history, waist circumference being greater than or equal to 95 cm, no target organ injury factor, no concomitant clinical disease, systolic blood pressure being 165 mmHg, and diastolic blood pressure being 102 mmHg, the temporary grade of the object may be determined as grade 2 based on systolic blood pressure and diastolic blood pressure, and the object is determined to have three other risk factors of the predetermined disease based on other risk factors of the predetermined disease (male, 56 years old, having smoking history, waist circumference being greater than or equal to 95 cm); and since the object has no target organ injury factor and no concomitant clinical disease, the grade of the object may be determined as high risk.

For example, whether there are respective risk factors (e.g., a cardiovascular risk factor), various target organ injuries, various clinical concomitant disease, diabetes, and chronic kidney disease (and a grade of chronic kidney disease) of predetermined disease may be determined at least based on at least one piece of physical sign data of the object and the predetermined medical rules; then the number of cardiovascular risk factors, target organ injuries, and clinical concomitant diseases involved in the object are comprehensively judged, to further automatically calculate the grade of the object (e.g., hypertensive cardiovascular risk grade stratification).

For example, the health managing method provided by at least one embodiment of the present disclosure may automatically calculate the grade of the object (e.g., automatically prejudge cardiovascular risk stratification), so the doctor may confirm the grade of the object acquired through automatic calculation and then output diagnosis, which, thus, can improve work efficiency of the medical worker. For example, the automatically calculated grade of the object may assist the medical worker (e.g., the doctor) in establishing a treatment goal and formulating a coping approach suggestion form (e.g., proposing a follow-up health plan).

For example, in step S130, the automatically generating a coping approach recommendation form includes automatically generating the recommended drug list; in this case, the health managing method further includes: connecting to the object information database, and acquiring the drug contraindication of the object (e.g., drugs that cannot be used due to allergies) from the object information database.

For example, the automatically generating a coping approach recommendation form includes step S1331 to step S1333. For example, step S1331 to step S1333 may be executed sequentially.

Step S1331: connecting to a drug information database to acquire an available drug list.

Step S1332: eliminating inapplicable drugs in the available drug list based on the concomitant clinical disease factor and the drug contraindication of the object, to acquire an applicable drug list.

For example, in step S1332, drugs that cannot be used due to concurrent diseases may be eliminated based on the concomitant clinical disease factor; drugs that cannot be used due to allergies may be eliminated based on drug contraindication, so that the recommended drugs will not endanger safety of the object.

Step S1333: determining the recommended drug list from the applicable drug list based on the grade of the object.

For example, when the grade of the object is high, in order to relieve symptoms of the object more quickly, more expensive specific drugs or drugs with greater side effects may be used. For example, when the grade of the object is low, milder drugs may be used to reduce side effects. For example, based on the recommended drug list, the medical worker may write a health prescription (e.g., the coping approach suggestion form) faster, which, thus, can improve efficiency of the medical worker; in addition, the recommended drug list may also be used to assist a medical worker with junior qualification to make better clinical decisions.

For example, in step S130, the automatically generating a coping approach recommendation form includes automatically generating a recommended diet plan list; in this case, the health managing method further includes: step S1341 and step S1342.

Step S1341: connecting to the object information database, and acquiring a gender of the object, an age of the object, a height of the object, a weight of the object, a diet preference of the object or a dietary taboo of the object from the object information database.

Step S1342: automatically generating the recommended diet plan list at least based on the gender of the object, the age of the object, the height of the object, the weight of the object, the diet preference of the object, the dietary taboo of the object or the health management influencing factor, or any combination of these factors.

For example, in step S1342, the automatically generating the recommended diet plan list at least based on the gender of the object, the age of the object, the height of the object, the weight of the object, the diet preference of the object, the dietary taboo of the object or the health management influencing factor includes step S201 to step S205.

Step S201: automatically determining the required intake amount of macronutrients and micronutrients for the object within a predetermined time range based on a gender of the object, an age of the object, a height of the object and a weight of the object.

Step S202: connecting to an ingredients information database to acquire an available ingredient list.

Step S203: eliminating inapplicable ingredients in the available ingredient list based on a dietary taboo of the object, to automatically acquire an applicable ingredient list.

For example, a dietary taboo of the object include dietary taboos caused by allergies, religious beliefs, or other factors.

Step S204: automatically determining an upper limit of intake of specified ingredients based on the concomitant clinical disease factor.

For example, if the object suffers from concomitant diabetes, daily sugar intake is restricted.

Step S205: automatically determining the recommended diet plan list from the applicable ingredient list based on the required intake amount of macronutrients and micronutrients for the object, the upper limit of intake of specified ingredients, and the diet preference of the object.

For example, the required intake amount of macronutrients and micronutrients for the object may be determined based on at least one selected from the group consisting of Chinese Dietary Guidelines (2016) and People's Republic of China Health Industry Standards. For example, whether nutrient contents of combination of ingredients satisfy the required intake amount of macronutrients and micronutrients for the object and whether the amount of specified ingredients in the combination of ingredients is less than the upper limit of intake of specified ingredients may be determined based on authoritative knowledge bases such as Chinese Food Composition Tables (2017).

For example, in a case where the nutrient contents of the combination of ingredients satisfy the required intake amount of macronutrients and micronutrients for the object and the amount of specified ingredients in the combination of ingredients is less than the upper limit of intake of specified ingredients, the above-described combination of ingredients that satisfies the requirements may be recommended to the object. For another example, in a case where the nutrient contents of the combination of ingredients satisfy the required intake amount of macronutrients and micronutrients for the object and the amount of specified ingredients in the combination of ingredients is less than the upper limit of intake of specified ingredients, a combination of meals (e.g., breakfast including fennel buns, eggs, and milk) may be generated based on the above-described combination of ingredients that satisfies the requirements (e.g., flour, meat, fennel, eggs, and milk).

FIG. 3 is a schematic diagram of a recommended diet plan list for a week automatically generated by using the health managing method provided by at least one embodiment of the present disclosure. For example, as shown in FIG. 3, the recommended diet plan list for a specified management cycle (e.g., one week) automatically generated by using the health managing method provided by at least one embodiment of the present disclosure includes a meal combination of daily breakfast, lunch and dinner in the specified management cycle. For example, breakfast on Monday may include "fennel buns", "soy milk" and "boiled eggs".

In some examples, required daily energy and nutrient intake amount for the object (e.g., the patient) may be automatically calculated based on at least a part of information below: Basal Metabolic Rate Formula, Chinese Dietary Guidelines (2016), People's Republic of China Health Industry Standards, authoritative knowledge bases such as Chinese Food Composition Tables (2017), automatically acquired information of height, age, weight, disease, region, diet preference, and religious belief of the object (e.g., the patient), which, thus, can provide personalized intelligent diet recommendation for disease.

For example, the recommended diet plan list includes recipes (e.g., meal combinations) for a specified management cycle (e.g., one week), and a daily recipe at least includes 3 meals (breakfast, lunch and dinner). For example, when providing a meal combination for each meal, it is also possible to provide weight and proportion of three major nutrients per meal, weight of each dish and weight of ingredients, and contents of trace elements in each meal.

For example, when automatically generating the recommended diet plan list, the Resting Energy Expenditure (REE) of the object may be automatically calculated based on a gender of the object, an age of the object, a height of the object, and a weight of the object. For example, resting energy expenditure calculation formulas below may be used to calculate resting energy expenditure M_REE of a male object and resting energy expenditure F_REE of a female object: M_REE=9.99 W+6.25 H−4.92 A+5, F_REE=9.99 W+6.25 H−4.92 A−161, where, W is weight (unit, kg), H is height (unit, cm), and A is age (unit, years). For example, required daily energy intake for the object may be determined at least based on resting energy expenditure of the object (e.g., based on resting energy expenditure and exercise energy expenditure).

For example, the recommended diet plan list may be automatically generated based on genetic algorithms. For example, steps below may be used to automatically generate the recommended diet plan list based on a genetic algorithm. Firstly, each meal or food in a meal library may be partitioned according to classification in diet; for example, each meal or food may be classified as breakfast, lunch, dinner, or fruit. Secondly, each meal or food in the meal library is coded to compose breakfast number-lunch number-dinner number-fruit number; these numbers are used to generate a coded population; and the coded population is used to represent all recommended recipe categories (e.g., daily meal combinations). Thirdly, nutrient status of the recommended recipe categories (e.g., daily meal combinations) is analyzed, and the recommended recipe categories (e.g., daily meal combinations) are assessed based on nutritional meal standards provided by dietitians. For example, the plan may be assessed according to proportions of protein, fat, and carbohydrate in a daily recipe, by using an assessment function; and a parent, that is, a recipe most in line with an assessment status in the assessment function, may be selected based on an assessment result. Fourthly, the above-described recipe (parent) most in line with the assessment status is used to perform cross-inheritance and mutation to produce a next generation of individuals, and the above-described steps of parental selection, cross-inheritance and mutation, as well as production of a next generation of individuals are executed many times, until the recipe in line with the recommendation requirements is found, inheritance is ended and the recipe in line with the recommendation requirements (e.g., the recipe recommended by the optimal solution previously acquired) is output. For example, each time cross-inheritance and mutation are performed, the optimal solution acquired through each cross-inheritance and mutation may be recorded.

For example, the doctor may adjust the recommended recipe (e.g., the meal combinations) for a specified management cycle (e.g., one week). For example, the doctor may select a meal from a diet library suitable for the object (e.g., the patient) to replace at least part of the meal in the recommended recipe (e.g., the meal combinations). For example, the doctor may communicate the adjusted recipe with the object, and after confirmation of the object, send the adjusted meal (e.g., via the server) to the object (e.g., the patient).

For example, in step S130, the automatically generating a coping approach recommendation form includes automatically generating a recommended exercise plan list; in this case, the health managing method further includes step S1351 and step S1352.

Step S1351: connecting to the object information database, and acquiring an exercise preference of the object from the object information database.

Step S1352: automatically generating the recommended exercise list at least based on the grade of the object, the exercise preference of the object and a predetermined exercise principle.

For example, the automatically generating a recommended exercise list at least based on the grade of the object, an exercise preference of the object and a predetermined exercise principle includes: automatically generating the recommended exercise list based on the grade of the object, an exercise preference of the object, an age of the object, a current disease age of the object, and the predetermined exercise principle.

For example, in step S1352, the automatically generating a recommended exercise list at least based on the grade of the object, an exercise preference of the object and a predetermined exercise principle includes step S211 to step S213.

Step S211: connecting to an exercise information database to acquire a candidate exercise list.

Step S212: selecting an applicable exercise list from the candidate exercise list at least based on the grade of the object and an exercise preference of the object. For example, when the grade of the object is high, avoid choosing intense exercise.

Step S213: automatically generating the recommended exercise list based on the predetermined exercise principle and the applicable exercise list. For example, in step S213, with respect to the hypertensive patient, the predetermined exercise principle may be set based on the exercise principle for the hypertensive patient recommended by Chinese Hypertension Prevention and Control Guidelines.

FIG. 4 is a schematic diagram of a recommended exercise plan list for a week automatically generated by using a health managing method provided by at least one embodiment of the present disclosure.

As shown in FIG. 4, the recommended exercise plan list for a week automatically generated by the health managing method provided by at least one embodiment of the present disclosure includes daily exercise combinations in a specified management cycle (e.g., one week).

A method for automatically generating the recommended exercise plan list for a week by the health managing method provided in at least one embodiment of the present disclosure will be exemplarily described below in conjunction with an example.

For example, the health managing method provided by at least one embodiment of the present disclosure may automatically output the object's BMI, exercise principle (exercise item, exercise intensity, exercise time, exercise frequency), the recommended exercise list of a specified management cycle, daily calories consumed by exercise in the specified management cycle and daily exercise proportioning in the specified management cycle according to an exercise principle of specified disease and the object's data below: gender (from app user information), age (from app user information,) height (from app user information), weight (from app user information, and physical examination reports), disease (from app questionnaire, and physical examination reports), exercise preference (from app questionnaire), waist circumference (from app user information), body fat rate (acquired from physical sign monitoring device or manually entered).

For example, the exercise principles for hypertensive patients recommended by Chinese Hypertension Prevention and Control Guidelines are as follows. Categories of exercise: hypertensive patients should perform continuous, rhythmic, aerobic exercise that mobilizes large muscle groups, supplemented by multi-part resistance training, and traction exercises after each exercise. Exercise intensity: medium intensity (40% to 59% Heart Rate Reserve (HRR)); Rating of Perceived Exertion (RPE), 12 to 13. Exercise time: aerobic exercise should last more than 30 min/d, if it needs to be done in stages, each stage should last no less than 10 min; resistance exercises with at least 8 to 10 different kinds of actions should be done, each group repeated 8 to 10 times, 2 to 4 groups repeated; static stretch should last 10 to 30 s, each action repeated 2 to 4 times. Exercise frequency: aerobic exercise should be done 5 to 7 days a week, resistance training 2 to 3 days a week, traction exercise at least 2 to 3 days a week; and it is suggested to do traction exercises after each exercise.

For example, exercise items suitable for the user may be automatically screened from the database based on at least a part of user information and exercise preferences (e.g., information acquired from an app lifestyle questionnaire), to acquire the recommended exercise list. For example, an exercise library contains: exercise items and exercise categories the exercise items belongs to (aerobic exercise, resistance exercise, anaerobic exercise), exercise intensity of exercise items, Metabolic Equivalents (METS) values of exercise items, and indications and contraindications of exercise items.

For example, energy that the user can consume after exercise following the recommended exercise list or exercise plan may be calculated based on the METS value of each exercise in the exercise database. For example, energy consumed by exercise may be calculated by using a formula below: male exercise expenditure (kcal)=(9.99 W+6.25

H−4.92 A+5)/1440*METS*exercise time; female exercise expenditure (kcal)=(9.99 W+6.25 H−4.92 A−161)/1440*METS*exercise time.

For example, the health managing method may further include: outputting the automatically generated coping approach recommendation form to a client (e.g., a medical worker client), and displaying the same on the client (e.g., the medical worker client).

For example, the health managing method may further include step S301 to step S302.

Step S301: receiving, from the client, coping approach recommendation form adjustment data generated according to a coping approach recommendation form adjustment operation.

For example, after completing a first visit to an object, a medical worker may execute a coping approach recommendation form adjustment operation based on information acquired from the first visit, so the client may receive the coping approach recommendation form adjustment data generated by the coping approach recommendation form adjustment operation, and supply the coping approach recommendation form adjustment data generated by the coping approach recommendation form adjustment operation to the client. The information acquired from the first visit includes: the object's acceptance for or opinion on the coping approach recommendation form.

For example, the medical worker may execute the coping approach recommendation form adjustment operation by clicking an operation "+" or an operation "−" in the coping approach recommendation form. For example, the medical worker may click on "+" shown in FIG. 4 to add exercise that the object prefers, and click on "−" shown in FIG. 4 to delete the exercise that the object does not like. For example, the coping approach recommendation form adjustment operation may be recalculating the grade of the object and automatically generating the coping approach recommendation form after a review operation is completed.

In one example, a single medical worker executes the coping approach recommendation form adjustment operation; and in another example, a plurality of medical workers execute the coping approach recommendation form adjustment operation.

Step S302: adjusting the coping approach recommendation form based on the coping approach recommendation form adjustment data, to generate the coping approach suggestion form.

For example, the coping approach suggestion form includes: at least one selected from the group consisting of a drug regimen, a diet plan, an exercise plan, and a management cycle. For example, the coping approach suggestion form also includes a management goal (e.g., to reduce systolic blood pressure from 180 to 150 mmHg).

In one example, the client (e.g., the medical worker client) may adjust the coping approach recommendation form based on the coping approach recommendation form adjustment data and generate the coping approach suggestion form; and the generated coping approach suggestion form is supplied to the server for storage; for example, the server may supply the coping approach suggestion form to the object client. For example, the server may supply the coping approach suggestion form to the medical worker client.

In another example, the server may adjust the coping approach recommendation form based on the coping approach recommendation form adjustment data and generate the coping approach suggestion form; for example, the server may supply the coping approach suggestion form to the object client and the medical worker client.

In some examples, the operation of adjusting, by the medical worker, the coping approach recommendation form based on the coping approach recommendation form adjustment data is also referred to as formulating or compiling, by the medical worker, the coping approach suggestion form (or a draft coping approach suggestion form).

Figure 5:
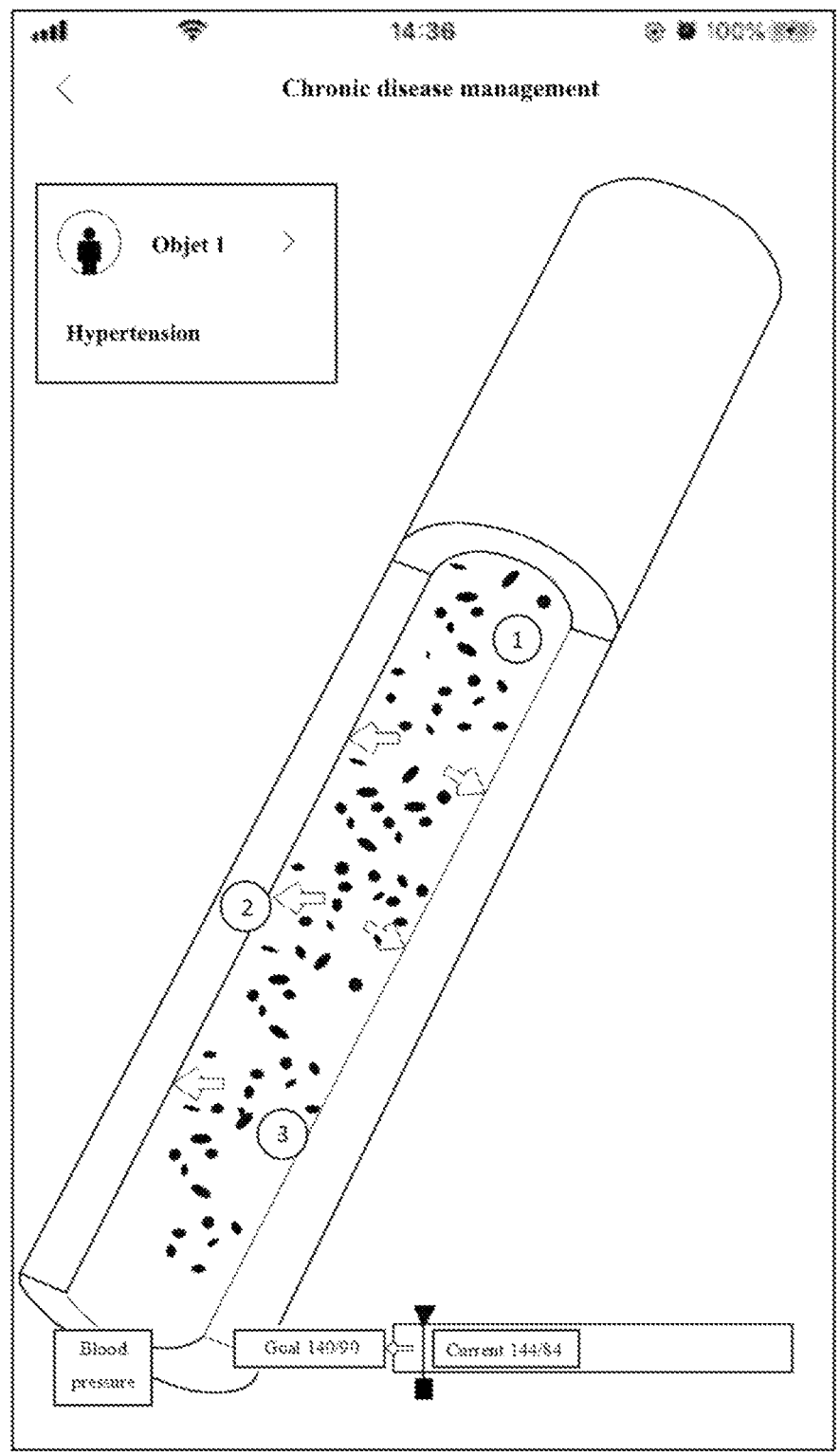
FIG. 5 shows a main interface for predetermined disease management of an object client provided by at least one embodiment of the present disclosure.

FIG. 5 shows a main interface of predetermined disease management of an object client provided by at least one embodiment of the present disclosure. For example, the object may intuitively see the object's current blood pressure, the object's blood pressure management goal, and 3D graphics of the object's blood vessels and blood from FIG. 5, so that the object may have a more intuitive and clear understanding of his/her own status and blood the pressure management goal.

Figure 6:
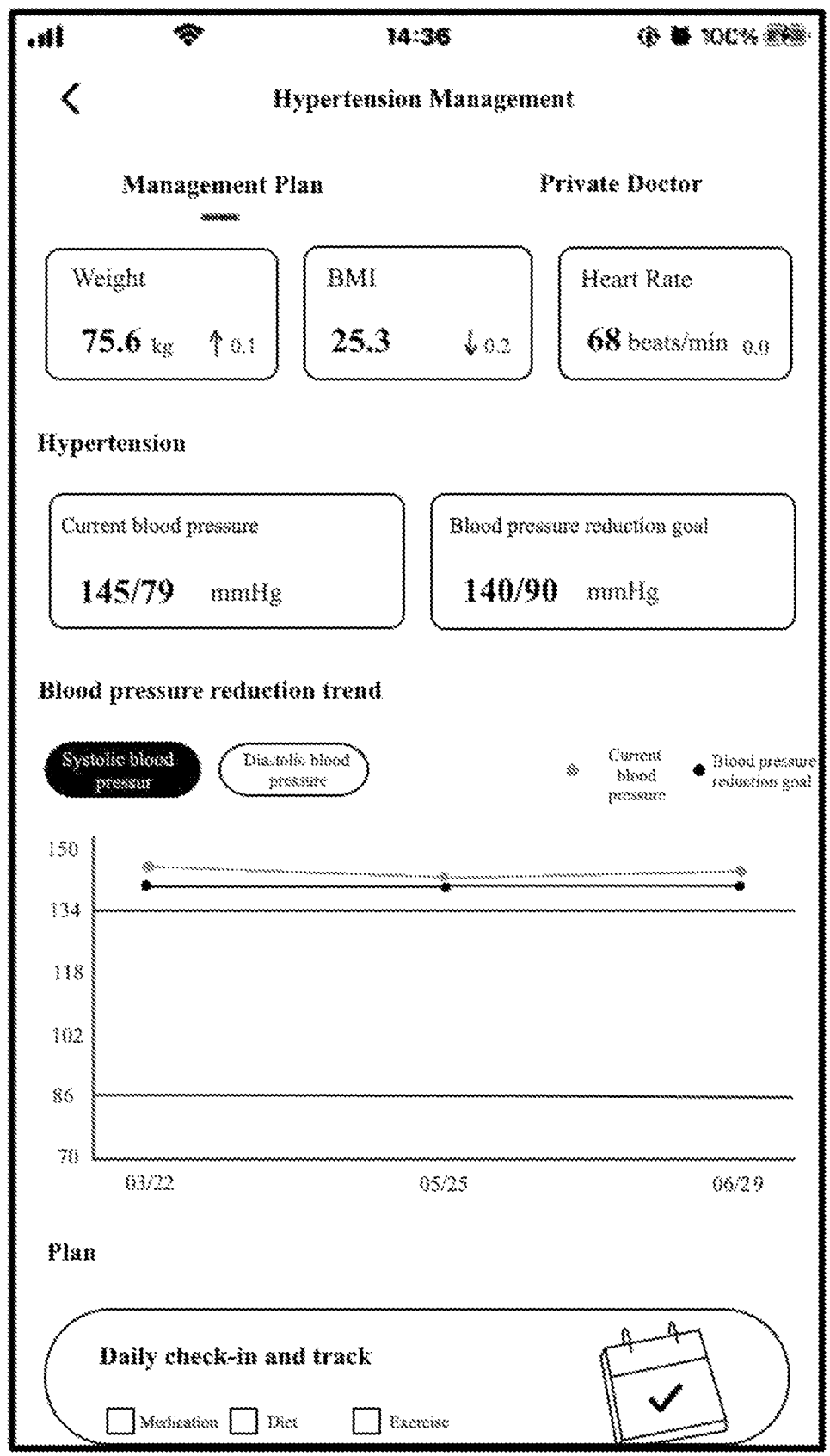
FIG. 6 shows a schematic diagram of a hypertension management plan shown by an object client provided by at least one embodiment of the present disclosure.

FIG. 6 shows a schematic diagram of a hypertension management plan displayed by an object client provided by at least one embodiment of the present disclosure. For example, as shown in FIG. 6, the object may see the object's current blood pressure and the management goal (e.g., a blood pressure reduction goal) from the object client.

For example, as shown in FIG. 6, the object may see a weight of the object (current weight), BMI (current BMI), and heart rate (current heart rate) from the object client. For example, as shown in FIG. 6, the object may see a curve of the object's blood pressure over time (i.e., an antihypertensive trend) from the object client, so that the object may clearly and intuitively understand changes (e.g., improvements) in his/her own blood pressure, thereby increasing motivation of the object to insist on implementing the coping approach suggestion form.

Figure 7:
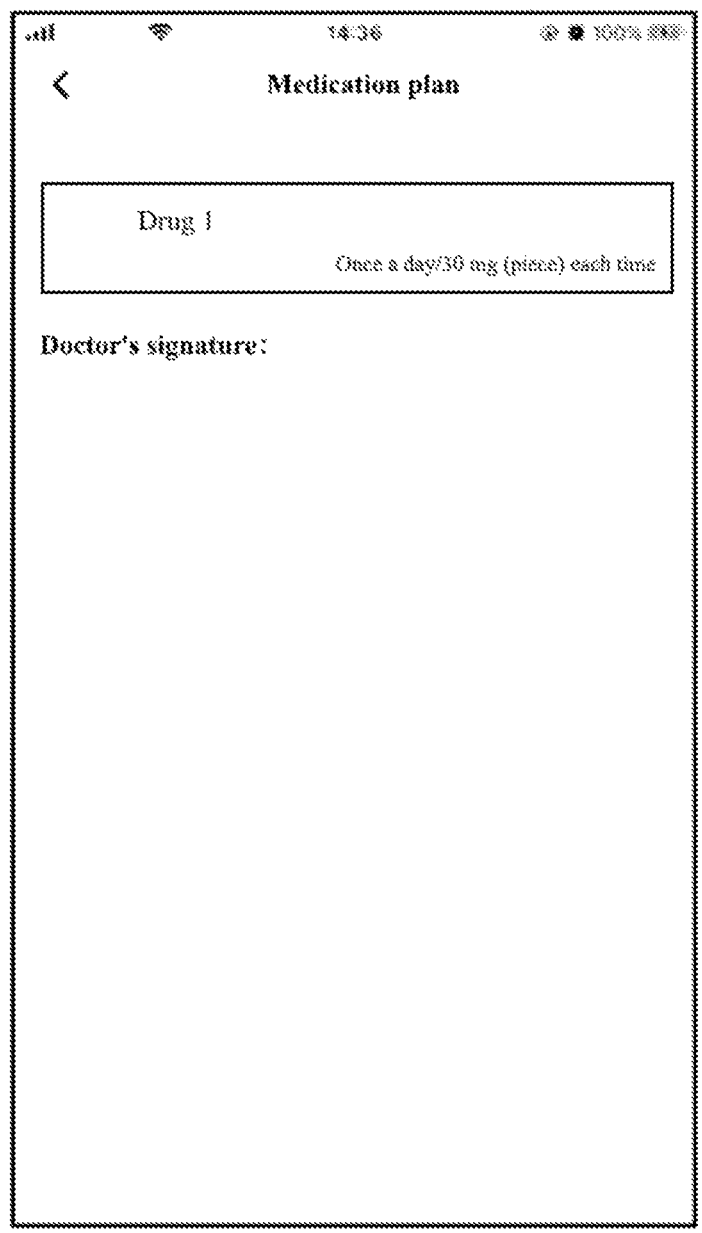
FIG. 7 shows a schematic diagram of a drug regimen shown by an object client provided by at least one embodiment of the present disclosure.

FIG. 7 shows a schematic diagram of a drug regimen (medication plan) displayed by an object client provided by at least one embodiment of the present disclosure. For example, as shown in FIG. 7, the drug regimen gives a name of a drug that the object needs to take each day, specifications of the drug, and the number of times to take each day.

Figure 8:
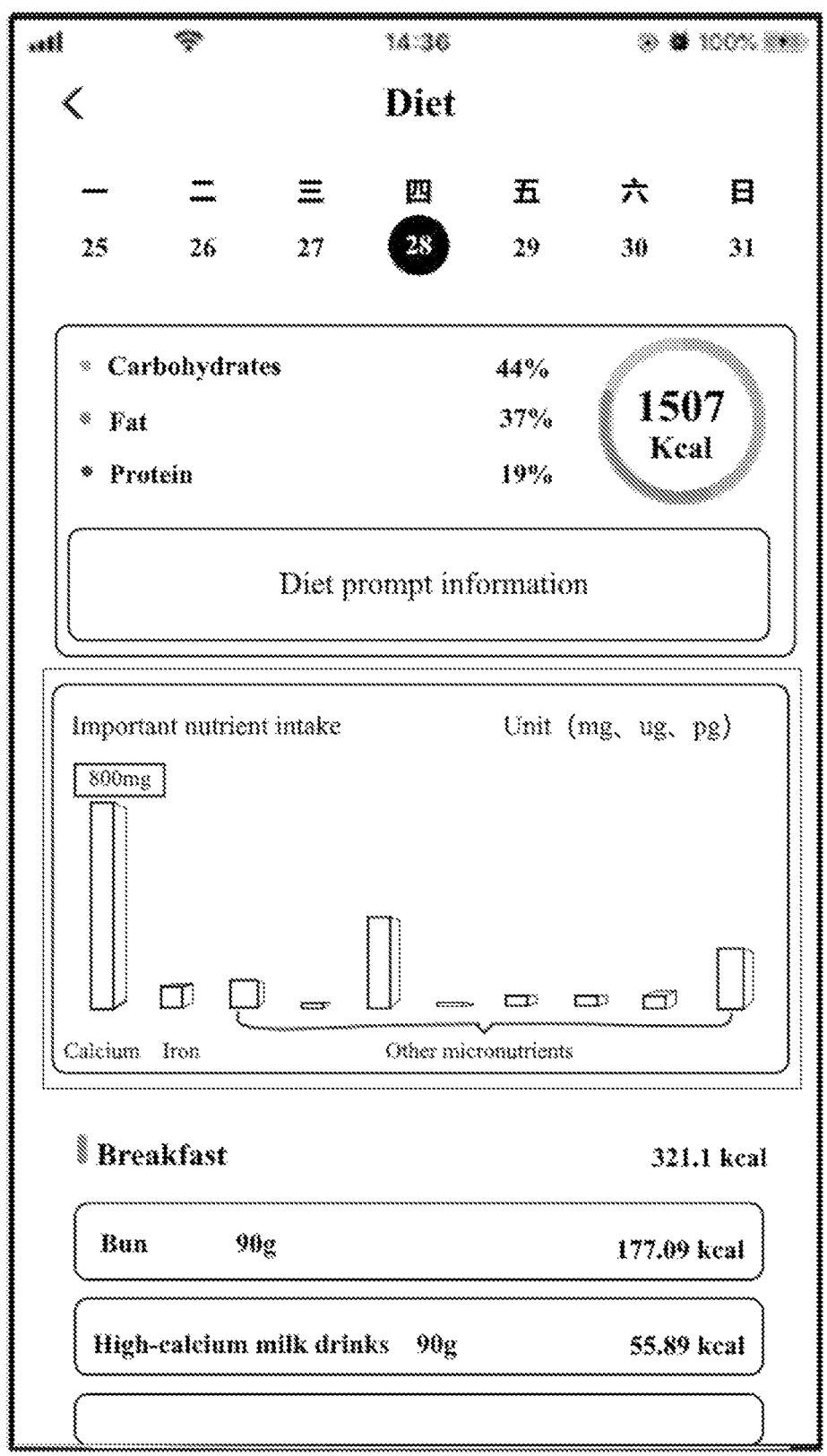
FIG. 8 shows a schematic diagram of a diet plan shown by an object client provided by at least one embodiment of the present disclosure.

FIG. 8 shows a schematic diagram of a diet plan (meal) displayed by an object client provided by at least one embodiment of the present disclosure. For example, as shown in FIG. 8, the diet plan gives the object's weekly breakfast, lunch and dinner recipes (that is, meal combinations). For example, by clicking on a date on the calendar, the object may see breakfast, lunch and dinner recipes (that is, meal combinations) on a specified date. For example, as shown in FIG. 8, breakfast on Thursday includes: steamed buns (90 g) and high-calcium milk drinks (90 g). For example, as shown in FIG. 8, the object client may also display calories, the amount of macronutrients (that is, carbohydrates, fat, and protein) and the amount of micronutrients (e.g., calcium, iron, zinc, vitamin A, B1, B12, etc.) included in each meal combination, as well as calories of each meal in each meal combination, for example, calories of 90 g steamed buns are 177.09 kcal.

For example, as shown in FIG. 8, the object client may also display diet prompt information for the patient with predetermined disease.

Figure 9:
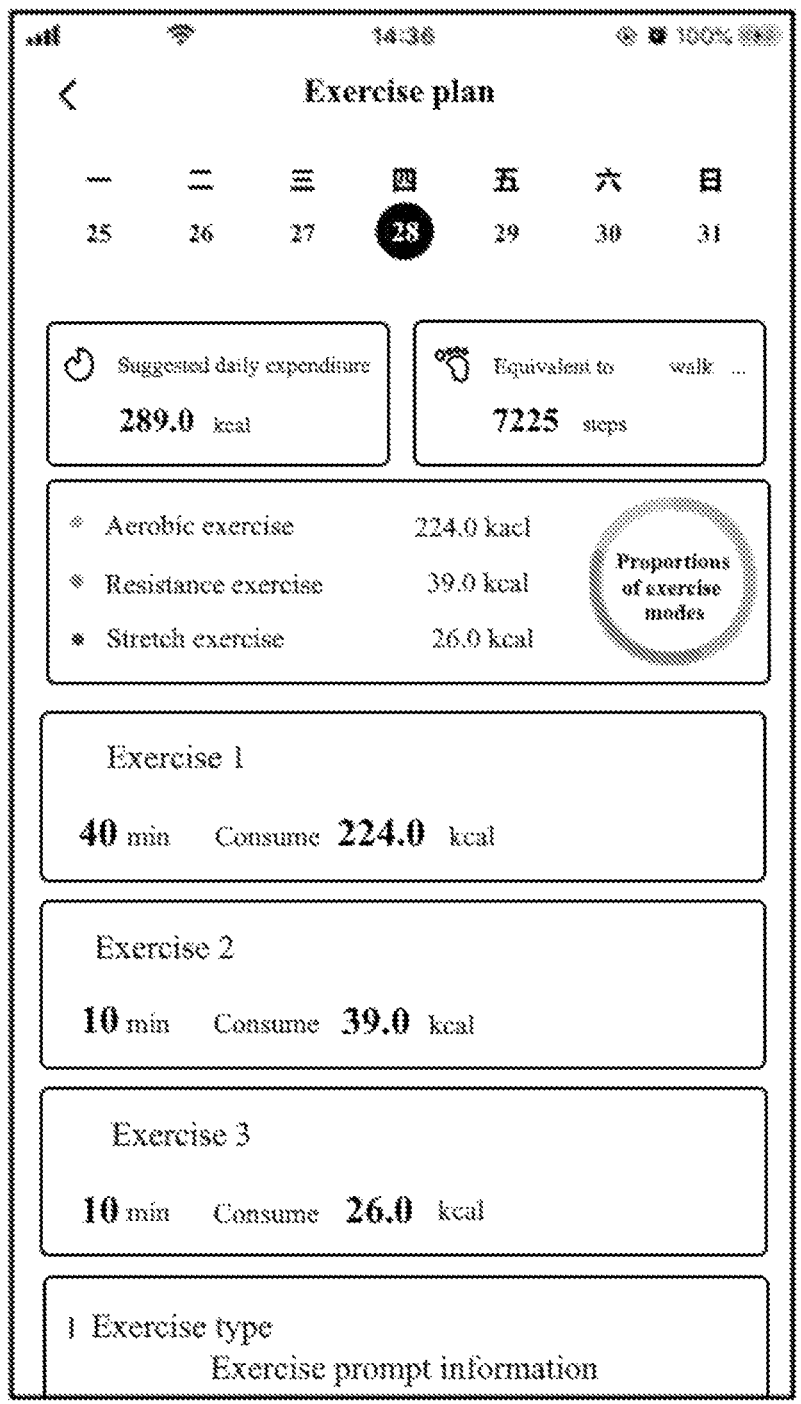
FIG. 9 shows a schematic diagram of an exercise plan shown by an object client provided by at least one embodiment of the present disclosure.

FIG. 9 shows a schematic diagram of an exercise plan displayed by an object client provided by at least one embodiment of the present disclosure. As shown in FIG. 9, the diet plan gives the object's weekly exercise combinations. For example, the object may see an exercise combination on a specified date and time of each exercise in the exercise combination by clicking on a date on the calendar. For example, as shown in FIG. 9, the exercise combination on Thursday includes: exercise 1: 40 minutes (min); exercise 2: 10 min; and exercise 3: 10 min. For example, exercise 1, exercise 2 and exercise 3 may respectively belong to aerobic exercise, resistance exercise, and stretch exercise. For example, as shown in FIG. 9, the object client may also display calories consumed by each exercise in the exercise combination. For example, as shown in FIG. 9, the object client may also display calories consumed by exercise of a specified exercise type in the exercise combination (e.g., calories consumed by aerobic exercise, resistance exercise, and stretch exercise). For example, as shown in FIG. 9, the object client may also display suggested daily calorie consumption and the number of steps corresponding to the suggested daily calorie consumption. For example, as shown in FIG. 9, the object client may also display exercise prompt information (e.g., exercise type prompt information).

For example, the health managing method further includes step S311 and step S312.

Step S311: receiving, from the client (e.g., the object client), execution confirmation data generated according to a coping approach suggestion form execution confirmation operation.

Figure 10:
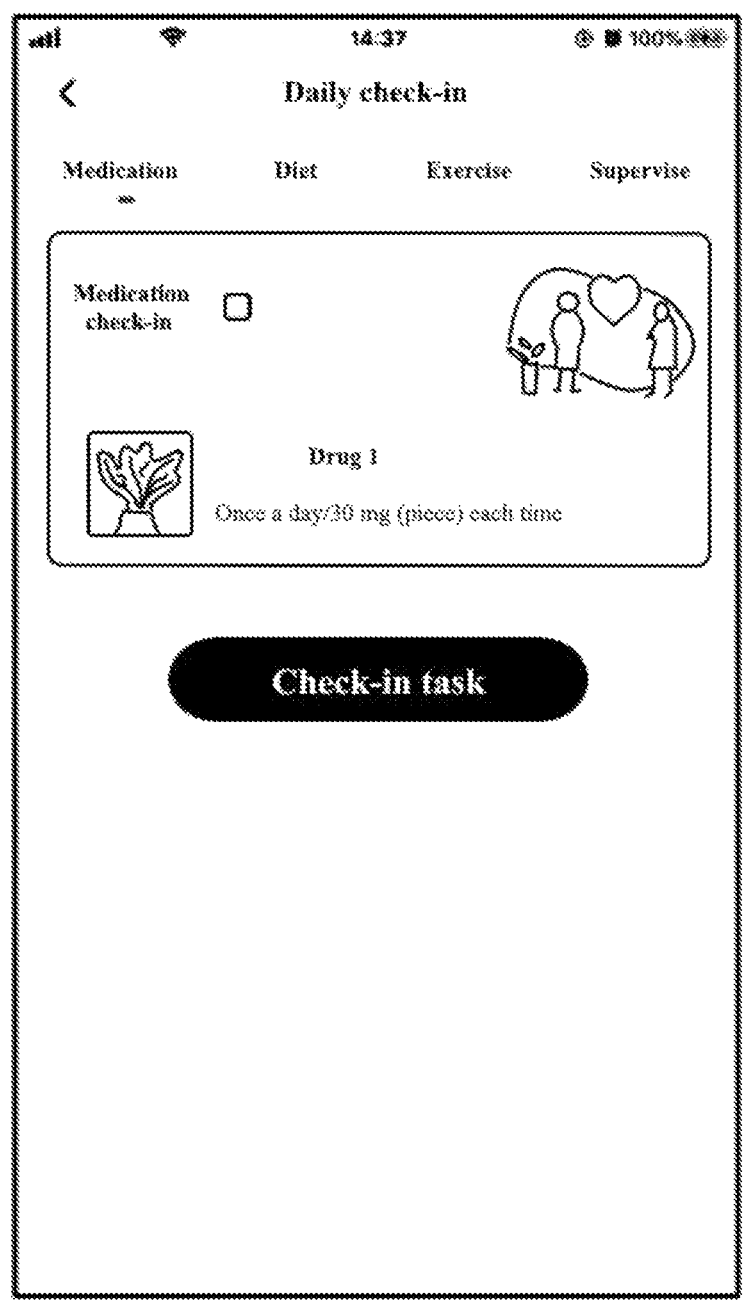
FIG. 10 shows a schematic diagram of a coping approach suggestion form execution confirmation interface included by an object client provided by at least one embodiment of the present disclosure.

FIG. 10 shows a schematic diagram of a coping approach suggestion form execution confirmation interface included by an object client provided by at least one embodiment of the present disclosure. For example, having executed the plan (e.g., the drug regimen) included in the coping approach suggestion form, the object may execute the suggestion form execution confirmation operation via the coping approach suggestion form execution confirmation interface (e.g., a check-in interface) included by the client shown in FIG. 10 (e.g., check a box after medication check-in shown in FIG. 10); correspondingly, the client receives the execution confirmation data (e.g., the drug regimen execution confirmation data) generated by the coping approach suggestion form execution confirmation operation, and supply the execution confirmation data generated by the coping approach suggestion form execution confirmation operation to the server.

For example, the execution confirmation data may include execution confirmation data of each plan of the coping approach suggestion form; for example, the execution confirmation data may include the drug regimen execution confirmation data, the diet plan execution confirmation data, and the exercise plan execution confirmation data. For example, with respect to each plan of the coping approach suggestion form, the object may execute a coping approach suggestion form execution operation once a day (e.g., check in once a day) to generate execution confirmation data for each plan of the coping approach suggestion form.

For another example, the execution confirmation data may include execution confirmation data of an overall plan of the coping approach suggestion form; in this case, the object will execute the coping approach suggestion form execution confirmation operation after completing all the plans corresponding to the day in the coping approach suggestion form every day.

For example, the coping approach suggestion form execution confirmation operation includes a medication plan execution confirmation operation, a diet plan execution confirmation operation, and an exercise plan execution confirmation operation. For example, the coping approach suggestion form execution confirmation operation may also include physical sign data monitoring execution confirmation operation.

Step S312: outputting, in response to not receiving the execution confirmation data from the client within a predetermined time period, a second alarm instruction.

For example, the predetermined time period may be a specified time period each day. For example, in a case of failure to receive all of the execution confirmation data (e.g., drug regimen execution confirmation data, diet plan execution confirmation data, and exercise plan execution confirmation data) from the client between 0:00 to 19:59 every day, the second Alarm instruction is output. For example, the above-described second alarm instruction may be output to the medical worker client, so that the medical worker may remind the object to insist on executing the coping approach suggestion form. For another example, the above-described second alarm instruction may be firstly output to the object client to automatically remind the object to insist on executing the coping approach suggestion form, and then in a case where the object still insists on not executing the coping approach suggestion form, output to the medical worker client, thereby allowing the medical worker to remind the object again to insist on executing the coping approach suggestion form, which, thus, can improve the object's compliance with the coping approach suggestion form.

Figure 11:
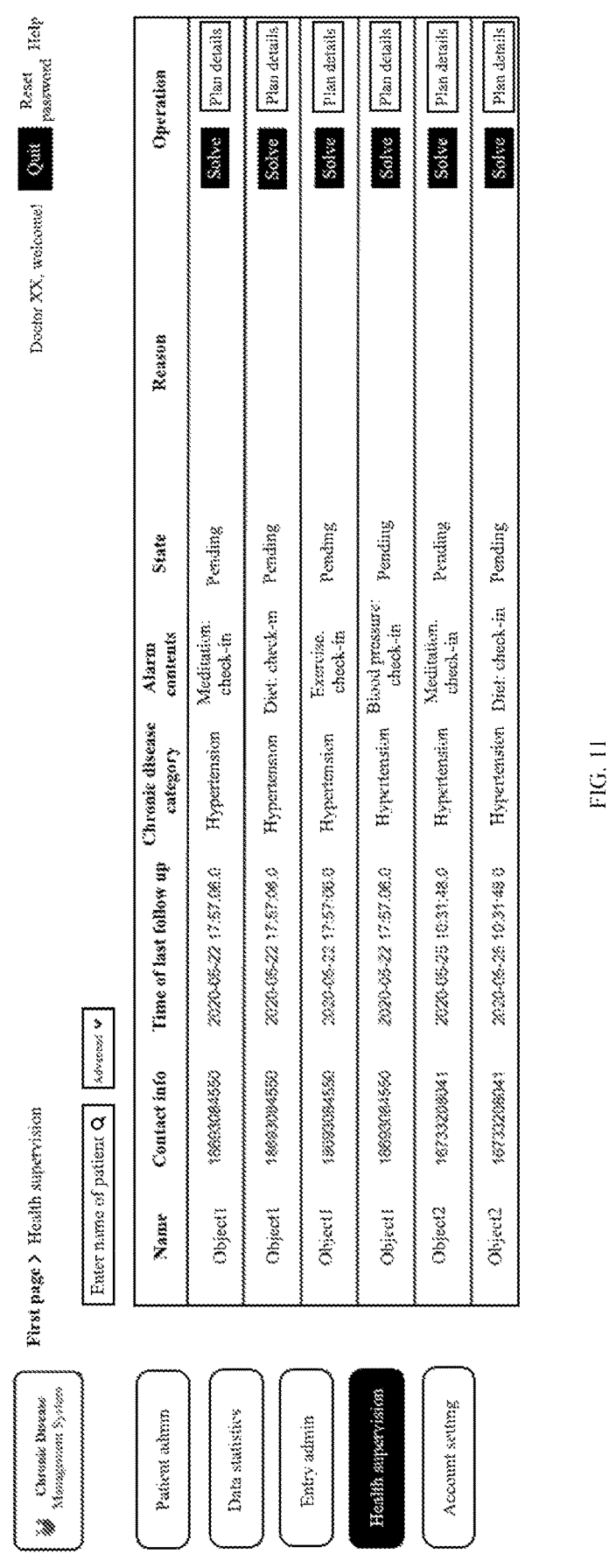

FIG. 11 is a schematic diagram of a health supervision page included by a medical worker client provided by at least one embodiment of the present disclosure. For example, the health supervision page shown in FIG. 11 displays an alarm (e.g., medication check-in, pending) for an object who fails to execute the coping approach suggestion form execution confirmation operation (e.g., check in) within predetermined time. In this case, the medical worker client may click a "Resolve" button corresponding to an "Operation" column to acquire contact information of the object, and remind the object to insist on executing specific items in the coping approach suggestion form through the client or phone.

For example, the health managing method further includes step S321 and step S322.

Step S321: receiving, from the client or a physical sign monitoring device used by the object, at least one piece of updated physical sign data of the object that is generated by the physical sign monitoring device used by the object.

Step S322: outputting, in response to the updated physical sign data being abnormal, a first alarm instruction.

For example, the object may use the physical sign monitoring device to acquire the physical sign data of the object. For example, the physical sign data of the object acquired by the physical sign monitoring device (acquired through detection) may be uploaded to the client; in this case, the at least one piece of updated physical sign data of the object that is generated by the physical sign monitoring device used by the object may be received from the client. For another example, the at least one piece of updated physical sign data of the object that is generated by the physical sign monitoring device used by the object may be directly received from the physical sign monitoring device used by the object.

For example, physical sign data being abnormal refers to that a value of the physical sign data indicates that the object is about to be in a dangerous state. For example, when a blood pressure value in the updated data is 189/100 mmHg, the server may output the first alarm instruction.

For example, in step S322, the server may output the first alarm instruction in response to the updated physical sign data being abnormal; and the above-described first alarm instruction may be supplied to the object client or the object's mobile phone (through text message), so the object may take timely measures when he/she is about to be a dangerous state, which further improves safety of the object.

For example, the above-described first alarm instruction may also be supplied to the medical worker client, so when the object is about to be in a dangerous state, the medical worker associated with the object may timely communicate with the object to confirm the state of the object, and provide professional coping approach suggestions to the object when the object is about to be in a dangerous state, which, thus, may further improve safety of the object.

For example, the physical sign monitoring device may be implemented as a smart terminal (e.g., a bracelet, a smart watch, smart glasses, smart shoes, a smart hat, smart clothing, etc.) or a home portable physical sign monitoring device (e.g., a home sphygmomanometer). For example, the physical sign monitoring device may acquire at least one piece of physical sign data (e.g., pulse, body temperature, heart rate, respiration, brain electricity, electrocardiogram, blood pressure, myoelectricity, etc.) of the detected object (e.g., patient).

For example, the health managing method further includes outputting a visit reminder (e.g., a follow-up reminder) based on a preset management cycle. For example, the visit reminder is output to the medical worker client, which, thus, can prevent the medical worker from forgetting and not being able to visit (e.g., follow up) the object according to the preset management cycle, and further allow the medical worker to follow the predetermined cycle to update and adjust the coping approach suggestion form.

Figure 12:
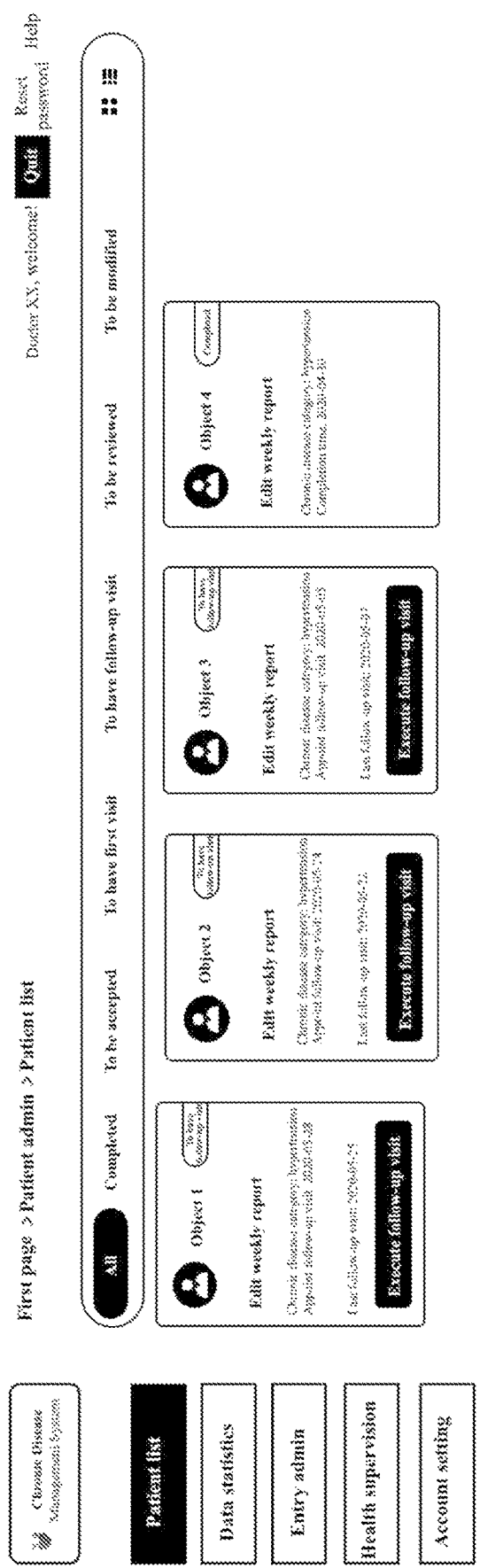
FIG. 12 shows an object list subpage of an object administration page included by a medical worker client provided by at least one embodiment of the present disclosure.

FIG. 12 shows an object (e.g., patient) list subpage of the object (e.g., patient) administration page included by a medical worker client provided by at least one embodiment of the present disclosure.

For example, the medical worker may click on "Pending Order" in the object (e.g., patient) list subpage shown in FIG. 12 to view the object assigned to the medical worker; after the medical worker confirms accepting the object, association is established between the object and the medical worker, whereby the medical worker may receive and view information of the object associated with him/her. For example, after the medical worker confirms accepting the object, the object will enter a "Pending First Visit" list shown in FIG. 12.

For example, the medical worker may click "Pending First Visit" on the object (e.g., patient) list subpage shown in FIG. 12 to view the object who needs a first visit. For example, during or after the first visit to the object, the medical worker adjusts the automatically generated coping approach recommendation form based on information acquired from the first visit, whereby the server or the client (e.g., the medical worker client) may adjust the coping approach recommendation form based on the coping approach recommendation form adjustment data to generate a coping approach suggestion form.

For example, the medical worker may click on "Pending Follow-up" in the object (e.g., patient) list subpage shown in FIG. 12 to view the object who needs a follow-up visit (e.g., revisit or non-first visit), and visit the object who needs a revisit. For example, during or before the revisit (e.g., follow-up visit) to the object, the medical worker may view the object's status in the last management cycle.

Figure 13:
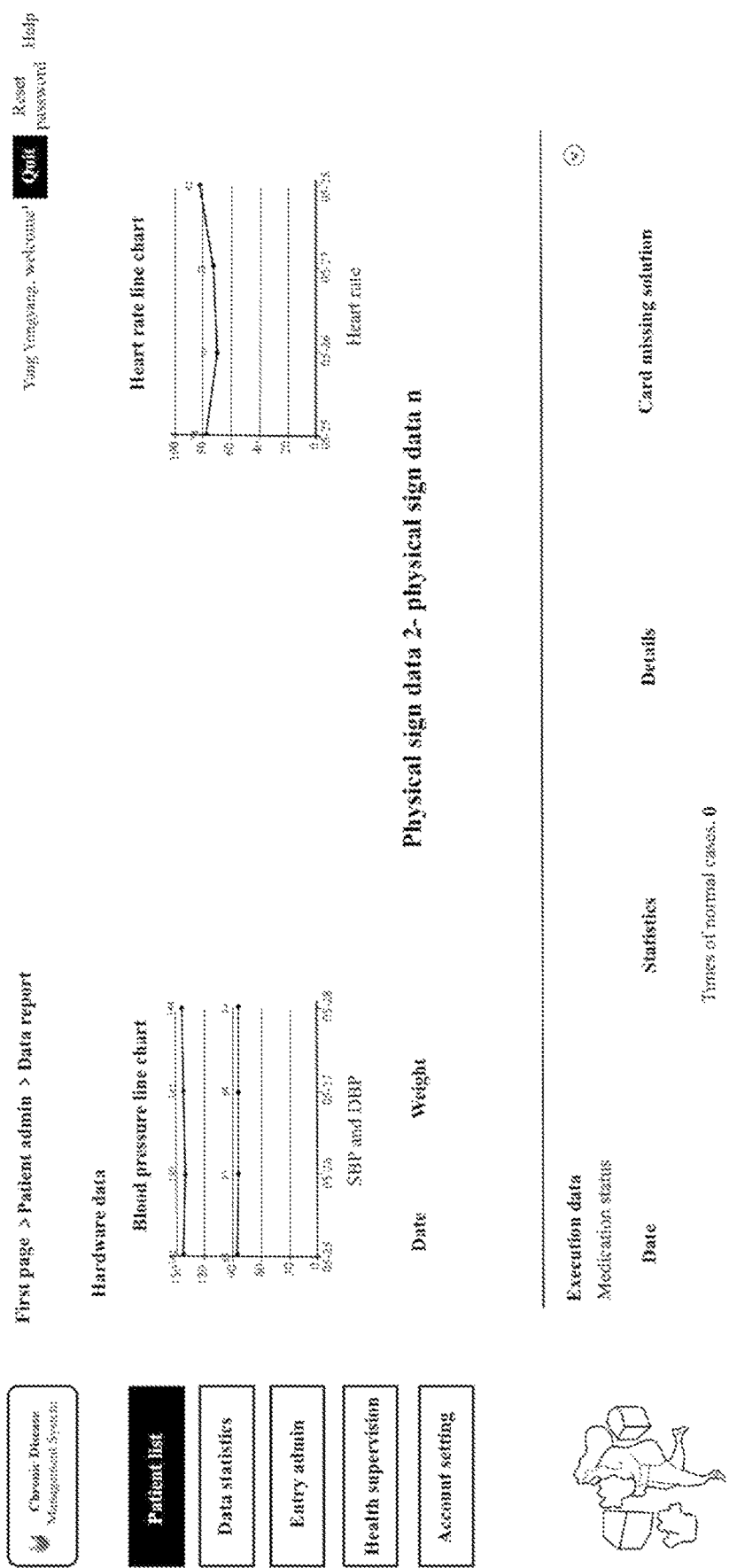
FIG. 13 shows a data report subpage of an object administration page included by a medical worker client provided by at least one embodiment of the present disclosure.

FIG. 13 shows a data report subpage of an object (e.g., patient) administration page included by a medical worker client provided by at least one embodiment of the present disclosure. For example, the medical worker may view the object's status in the last management cycle through a data report subpage of the object (e.g., patient) administration page shown in FIG. 13. For example, via the data report subpage of the object (e.g., patient) administration page shown in FIG. 13, changes of the physical sign data of the object over time in the last management cycle (i.e., hardware data shown in FIG. 13) and the object's last coping approach suggestion form execution data may be viewed. For example, the physical sign data of the object in the last management cycle and the object's last coping approach suggestion form execution data may be displayed in a form of table or graph. For example, the coping approach suggestion form execution data includes execution data of respective plans (e.g., the medication plan) included in the coping approach suggestion form.

For example, the health managing method further includes step S331 and step S332.

Step S331: receiving, from the client (e.g., the medical worker client), the coping approach suggestion form adjustment data generated according to the coping approach suggestion form adjustment operation.

Step S332: updating the coping approach recommendation form based on the coping approach suggestion form adjustment data.

For example, step S331 and step S332 may be executed during or after the follow-up visit to the object by the medical worker. For example, the medical worker may make a follow-up visit to the object at the end of each management cycle. For example, during the follow-up visit to the object, the medical worker may acquire information about the object in the last (or current) management cycle. For example, the information of the object in the last management cycle includes: the object's clinical symptoms (e.g., changes in the object's disease condition) in the last management cycle, the object's medication status (actual medication status, adverse drug reactions, and medication compliance) in the last management cycle and the object's lifestyle (e.g., actual diet and exercise status) in the last management cycle.

For example, the medical worker may assess relevance between the object's medication status and lifestyle in the last management cycle and the object's clinical symptom change in the last management cycle, and adjust the coping approach suggestion form (e.g., at least one selected from the group consisting of diet, exercise, and medication plan) for the last (or current) management cycle; and in this case, the client (e.g., the medical worker client) may receive the coping approach suggestion form adjustment data generated according to the coping approach suggestion form adjustment operation.

For example, the client (e.g., the medical worker client) may supply the coping approach suggestion form adjustment data generated according to the coping approach suggestion form adjustment operation to the server; the server may update the coping approach recommendation form based on the coping approach suggestion form adjustment data. For example, the coping approach suggestion form adjustment data may be an updated coping approach recommendation form, and in this case, the server may update the coping approach recommendation form by overwriting the coping approach recommendation form before adjustment with the updated coping approach recommendation form.

For example, the updated coping approach recommendation form may be supplied to the medical worker client; after another medical worker (a higher-level medical worker) approves, the updated coping approach recommendation form may be supplied to the object client. For example, after another medical worker rejects the updated coping approach suggestion form, the object will be included in a "to-be-modified" object list shown in FIG. 12. For example, the medical worker may further adjust the coping approach suggestion form, and the client (e.g., the medical worker client) may receive the coping approach suggestion form adjustment data generated according to the coping approach suggestion form adjustment operation, and supply the coping approach suggestion form adjustment data generated according to the coping approach suggestion form adjustment operation to the server; the server may further update the coping approach recommendation form based on the coping approach suggestion form adjustment data, and supply the further updated coping approach recommendation form to the medical worker client, waiting for another medical worker (a higher-level medical worker) to review. For example, the medical worker may adjust the coping approach suggestion form many times until another medical worker (a higher-level medical worker) approves, so the server may supply the updated coping approach suggestion form to the object client.

For example, by timely adjusting the coping approach suggestion form based on the object's disease condition changes, applicability of the coping approach suggestion form can be improved, the object's compliance and initiative can be improved, and time required for the object to heal can also be reduced.

For example, the medical worker may enter a follow-up plan generation and confirmation page after confirming the physical sign data of the object in the last management cycle shown in FIG. 13, so as to adjust the coping approach suggestion form of the last management cycle.

For example, the health managing method further includes step S341 and step S342.

Step S341: receiving, from the client, visit data generated according to a visit status filling operation.

Step S342: automatically generating a health stage summary at least based on the visit data.

For example, after the follow-up visit, the medical worker may fill in comments (e.g., comments on condition changes and coping approach suggestion form execution status of the object in the last management cycle) according to the visit status and guiding suggestions (e.g., guiding suggestions for a next management cycle); the client (e.g., the medical worker client) may receive the visit data generated according to the visit status filling operation, and supply the visit data generated according to the visit status filling operation to the server. For example, the server may automatically generate a health stage summary (e.g., a health weekly report) at least based on the visit data.

Figure 14:
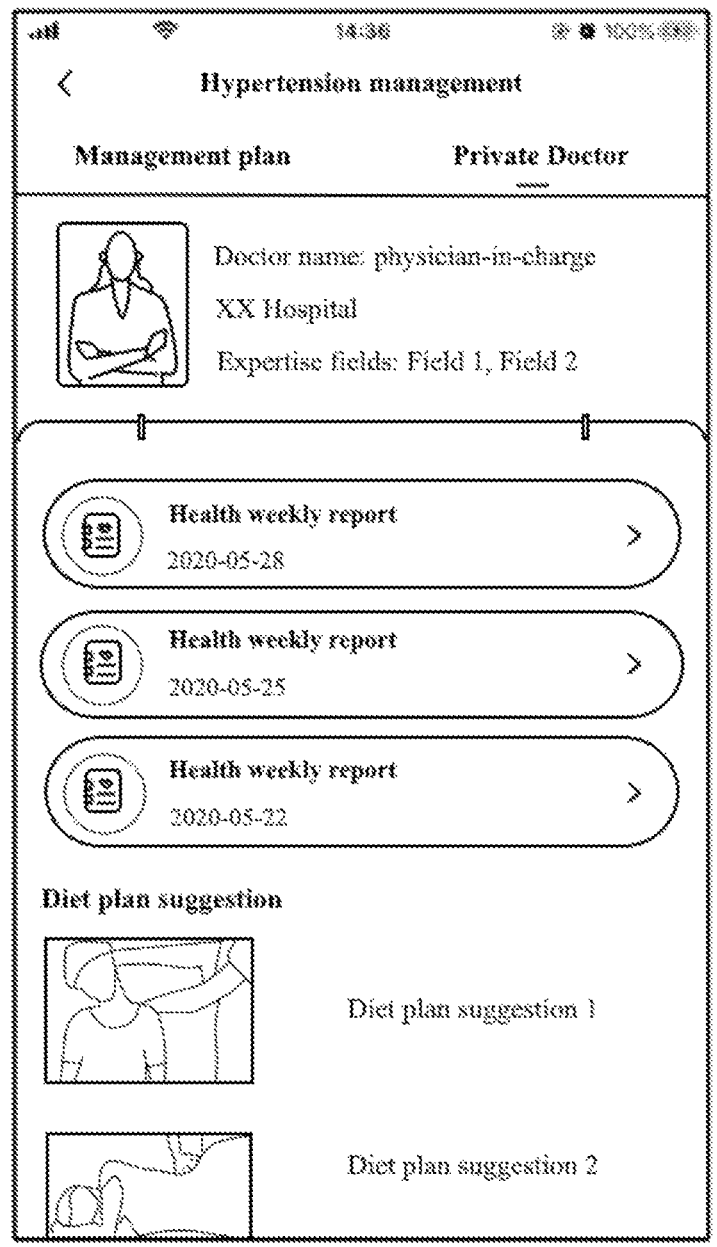
FIG. 14 shows a schematic diagram of a private doctor interface included by an object client provided by at least one embodiment of the present disclosure.

For example, the health stage summary (e.g., the weekly health report) may be supplied to the client (e.g., the object client), and the object may view the health stage summary by clicking "Health Weekly Report" on a "Private Doctor" interface shown in FIG. 14.

For example, the health stage summary may perform data visualization on a management result of the object in the last cycle, and attach comments and suggestions from the medical worker, which, thus, can improve stickiness between the object and the medical worker as well as enthusiasm for participating in management.

For example, the health managing method further includes receiving, from the client (e.g., the medical worker client), entry editing data generated according to an entry editing operation, and updating the entry database based on the entry editing data.

FIG. 15 shows a schematic diagram of an entry administration subpage included by a medical worker client provided by at least one embodiment of the present disclosure.

For example, the medical worker may edit his/her preferred entry (e.g., a drug entry or a supervision entry) on the entry administration subpage included by the client (e.g., the medical worker client) shown in FIG. 15, whereby the client (e.g., the medical worker client) may receive the entry editing data generated according to the entry editing operation, and supply the entry editing data generated according to the entry editing operation to the server, and then the server updates the entry database based on the entry editing data, for example, updates a part of the entry database that corresponds to the medical worker.

For example, by making the health managing method further include receiving, from the client (e.g., the medical worker client), entry editing data generated according to the entry editing operation, and updating the entry database based on the entry editing data, efficiency of the medical worker may be further improved. For example, when adjusting the coping approach recommendation form and the coping approach suggestion form, the medical worker may directly quote entries stored in the entry database that are frequently used by the medical worker. For another example, when reminding the object to insist on supporting the coping approach suggestion for, the medical worker may directly quote a supervision entry stored in the entry database that is frequently used by him/her.

For example, the health managing method further includes: performing, in response to a statistical data viewing operation received from the client (e.g., the medical worker client), data statistics on specified data, and generating and outputting a statistical result of the specified data. For example, the specified data statistical result may be grade distribution of objects associated with the medical worker and gender distribution of objects belonging to a certain grade (objects associated with the medical worker). For example, the data statistical result is supplied to the client (e.g., the medical worker client).

Figure 16:
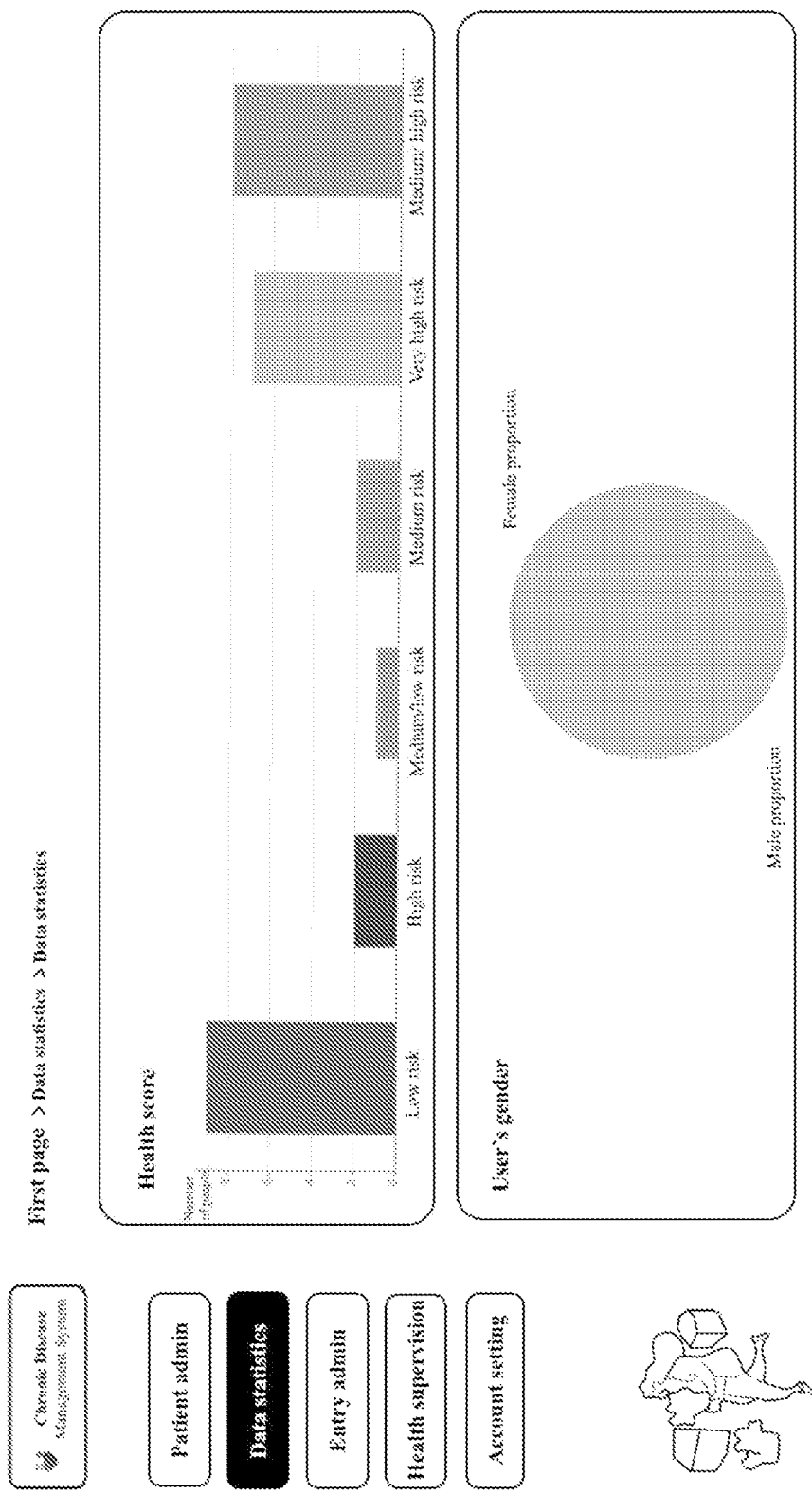
FIG. 16 shows a schematic diagram of a data statistical result subpage included by a medical worker client provided by at least one embodiment of the present disclosure.

FIG. 16 shows a schematic diagram of a data statistical result subpage included by a medical worker client (e.g., a medical worker client) provided by at least one embodiment of the present disclosure. For example, the client (e.g., the medical worker client) may display the specified data statistical result in a form of chart or graph.

For example, by making the health managing method further include: performing, in response to a statistical data viewing operation received from the client (e.g., the medical worker client), data statistics on specified data, and generating and outputting a statistical result of the specified data, the medical worker can more clearly and intuitively understand status of the user associated with him/her, so that the medical worker can allocate time and energy reasonably, which can further improve service quality of the medical worker and experience of the object.

For example, the health managing method further includes: receiving, from the medical worker client, information update data generated according to an information update operation, and updating the medical worker information database based on the information update data generated according to the information update operation.

Figure 17:
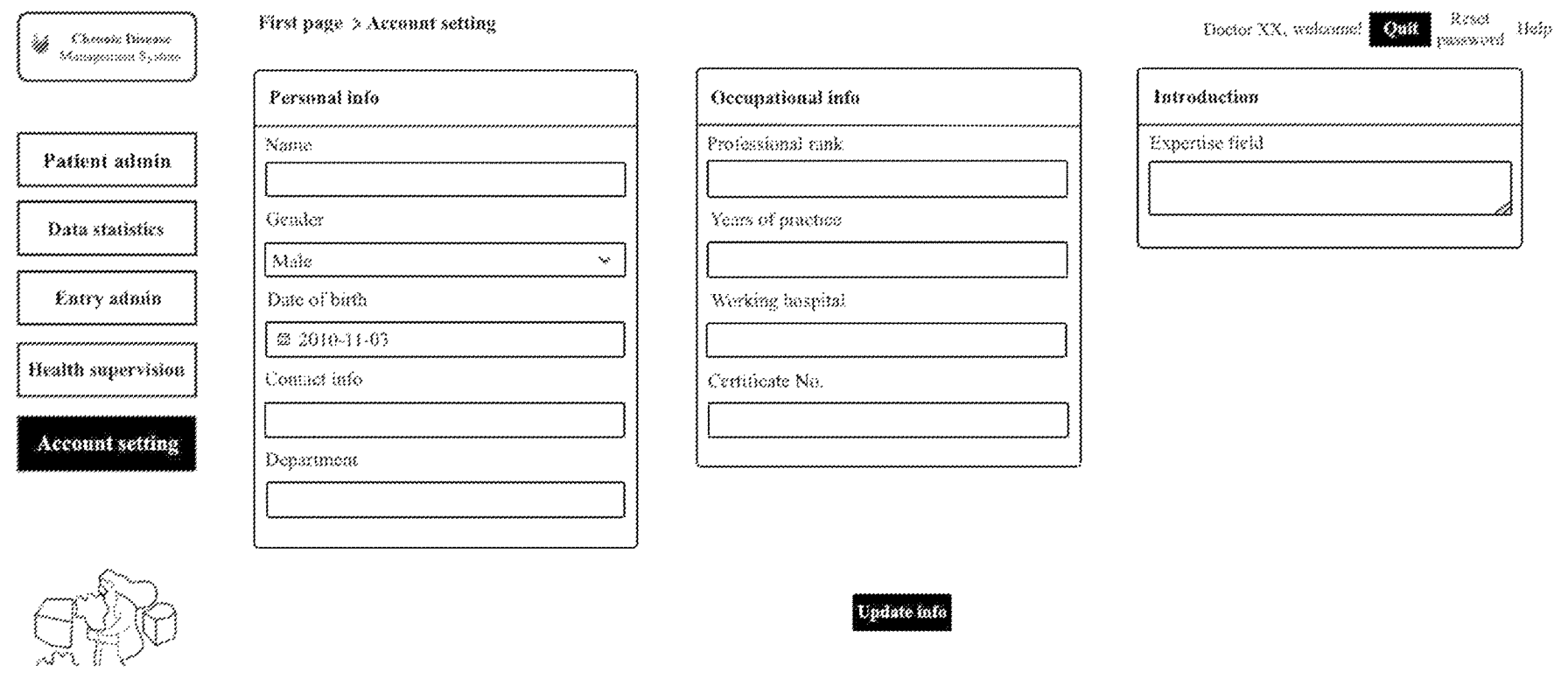

FIG. 17 shows a schematic diagram of an account setting subpage included by a medical worker client provided by at least one embodiment of the present disclosure. For example, the medical worker may set and update personal information via the account setting subpage, so that the medical worker client receives the information update data generated according to the information update operation, and supply the information update data generated according to the information update operation to the server; and the server updates the information data of the medical worker based on the information update data. For example, the updated information data of the medical worker is supplied to the object client. For example, the object may see the updated information data of the medical worker from the "Private Doctor" interface shown in FIG. 14, so that the object may timely learn the latest information of the doctor associated with him/her.

Figure 18:
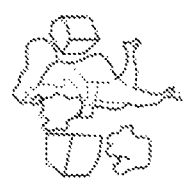
FIG. 18 shows a schematic diagram of an object administration subpage included by an administrator client provided by at least one embodiment of the present disclosure.

FIG. 18 shows a schematic diagram of an object (e.g., patient) administration subpage included by an administrator client provided by at least one embodiment of the present disclosure. For example, an administrator (e.g., a medical worker administrator) may assign an unassigned object to a doctor via the object (e.g., patient) administration subpage shown in FIG. 18. For example, the administrator may withdraw the assignment operation via the object administration subpage shown in FIG. 18, and reassign a medical worker to the object corresponding to the withdrawal operation. For example, the administrator may view at least one selected from the group consisting of a list of objects to be assigned, a list of objects having completed, a list of objects to be accepted, a list of objects to have a first visit, a list of objects to have a follow-up visit, a list of objects to be reviewed, and a list of objects to be modified via the object administration subpage shown in FIG. 18.

For example, the list of objects to be assigned includes objects currently unassigned to a specific medical worker. For example, the health managing method further includes: receiving, from the administrator client, object assignment data generated according to an object assignment operation, and pre-associating the object with a specified medical worker based on the object assignment data. For example, the "pre-associating the object with a specified medical worker" refers to allowing the medical worker to view relevant information of the object within a predetermined time period.

For example, the list of objects to be accepted includes objects having been assigned to a specific medical worker but have not yet been accepted by the specific medical worker. For example, the health managing method further includes: receiving, from the medical worker client, object acceptance data generated according to an object acceptance operation, and associating the medical worker with the accepted object based on the object acceptance data. For example, the medical worker may execute an object acceptance operation via the patient list subpage shown in FIG. 12, so that the medical worker client may receive the object acceptance data generated according to the object acceptance operation, and supply the object acceptance data generated according to the object acceptance operation to the server, and the server associates the medical worker with the accepted object based on the object acceptance data. For example, after associating the medical worker with the accepted object, the medical worker may view relevant information of the accepted object, and the accepted object may view relevant information of the medical worker.

For example, the list of objects having completed includes a list of objects who have completed health management for a specified period; that is, the list of objects having completed includes objects who previously participated in health management, but currently do not participate in health management for the time being.

For example, the list of objects to have a first visit includes: objects having been accepted by medical workers but the medical workers have not executed a first visit; the list of objects to have a follow-up visit includes: objects having participated in a first visit but not participated in a follow-up visit of a next management cycle; with respect to objects in the list of objects to be reviewed, the medical workers have formulated a draft coping approach suggestion form, but the draft has not yet been reviewed (not reviewed by another medical worker); with respect to objects in the list of objects to be modified, the coping approach suggestion form draft formulated by a medical worker is not approved, and another medical worker has given modification suggestions, but the medical worker has not yet modified the draft coping approach suggestion form.

For example, the health managing method further includes: acquiring, in response to a browsing operation of an object list of a specified type, an object list of a specified type from the object database, and supplying the object list of the specified type to the administrator client. For example, the object list of the specified type includes at least one selected from the group consisting of the list of objects to be assigned, the list of objects having completed, the list of objects to be accepted, the list of objects to have a first visit, the list of objects to have a follow-up visit, the list of objects to be reviewed, and the list of objects to be modified.

For example, by making the health managing method further include: acquiring, in response to a browsing operation of an object list of a specified type, an object list of a specified type from the object database, and supplying the object list of the specified type to the administrator client, the administrator can more clearly understand current distribution of objects and work saturation of medical workers, so that the administrator can assign objects more reasonably.

FIG. 19 shows a schematic diagram of an entry administration subpage included by an administrator client provided by at least one embodiment of the present disclosure.

For example, the medical worker administrator may edit his/her preferred entry (e.g., a drug entry or a supervision entry) on the entry administration subpage included by the administrator client shown in FIG. 19, whereby the administrator client may receive the entry editing data generated according to the entry editing operation, and supply the entry editing data generated according to the entry editing operation to the server, and then the server updates the entry database based on the entry editing data, for example, updates a part of the entry database that corresponds to the medical worker administrator.

For example, by making the health managing method further include receiving, from the administrator client, the entry editing data generated according to the entry editing operation, and updating the entry database based on the entry editing data, efficiency of the medical worker administrator may be further improved. For example, when reviewing the draft coping approach suggestion form formulated by the medical worker, the medical worker administrator may directly quote, for example, a drug entry in modification suggestions, which, thus, can improve communication efficiency between the medical worker administrator and the medical worker. For another example, the medical worker administrator may also directly quote an entry to adjust the draft coping approach suggestion form formulated by the medical worker. For another example, the medical worker administrator may also undertake tasks of serving an object and adjusting the coping approach recommendation form (formulating the coping approach suggestion form), and in this case, the medical worker administrator may directly quote an entry to adjust the coping approach recommendation form, which, thus, can improve efficiency of the medical worker administrator in adjusting the coping approach recommendation form.

It should be noted that, in some examples, the administrator client may not include the entry administration subpage.

For example, the health managing method further includes: supplying, in response to an approval instruction output by the administrator client, the coping approach suggestion form corresponding to the approval instruction to the object client. Exemplary description will be given below in conjunction with FIG. 20.

Figure 20:
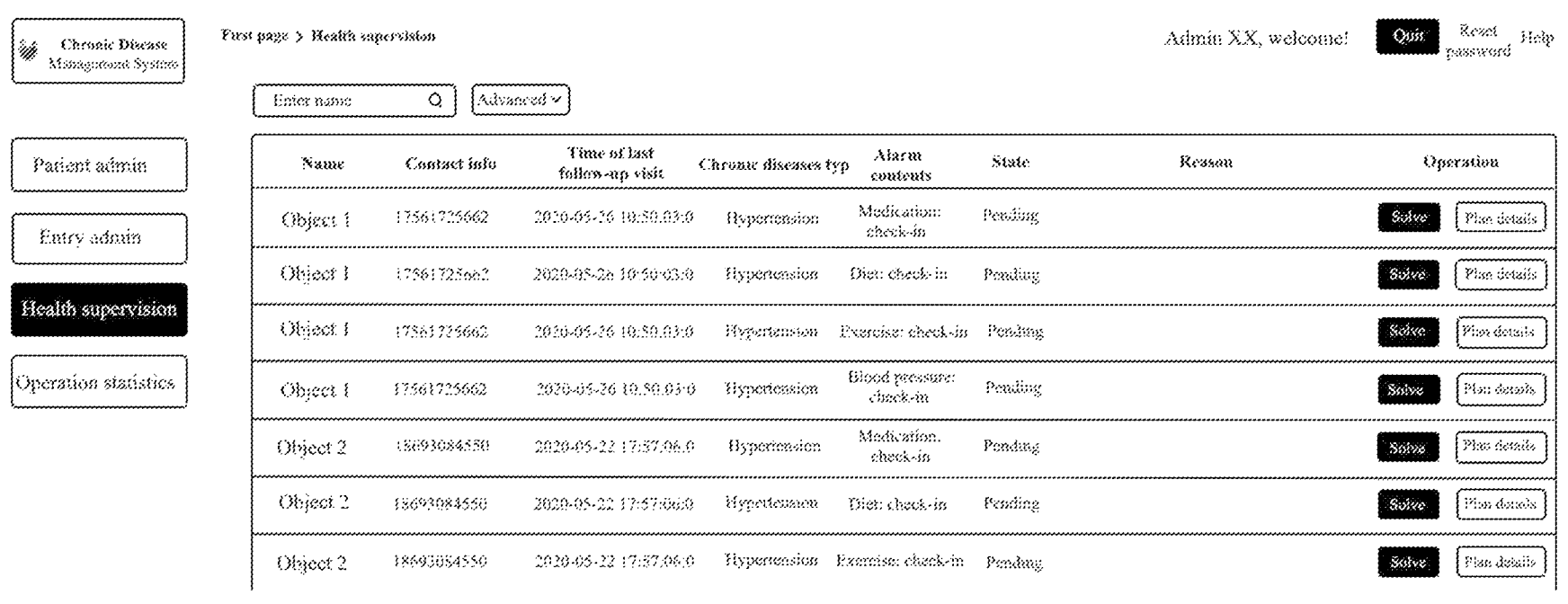

FIG. 20 shows a schematic diagram of a health supervision subpage included by an administrator client provided by at least one embodiment of the present disclosure. For example, on the health supervision subpage, the administrator may review whether the coping approach suggestion form provided by the medical worker (e.g., the health management plan) is reasonable.

For example, the administrator may view (e.g., view by clicking "Plan Details") the draft coping approach suggestion form formulated by the medical worker in the health supervision subpage included by the administrator client shown in FIG. 20; for example, when the draft coping approach suggestion form is applicable to the object, click an "Approved" button on the "Plan Details" page; and for example, when the draft coping approach suggestion form is inapplicable to the object, click a "Resolve" button and enter modification suggestions.

For example, the health managing method further includes: receiving, from the administrator client, an operation statistics request data generated according to an operation statistics request, performing statistics on operation data based on the operation statistics request data, and supplying an operation data statistics result to the administrator client. For example, the operation data includes: daily new objects, weekly new objects, monthly new objects, or other suitable operation data.

Figure 21:
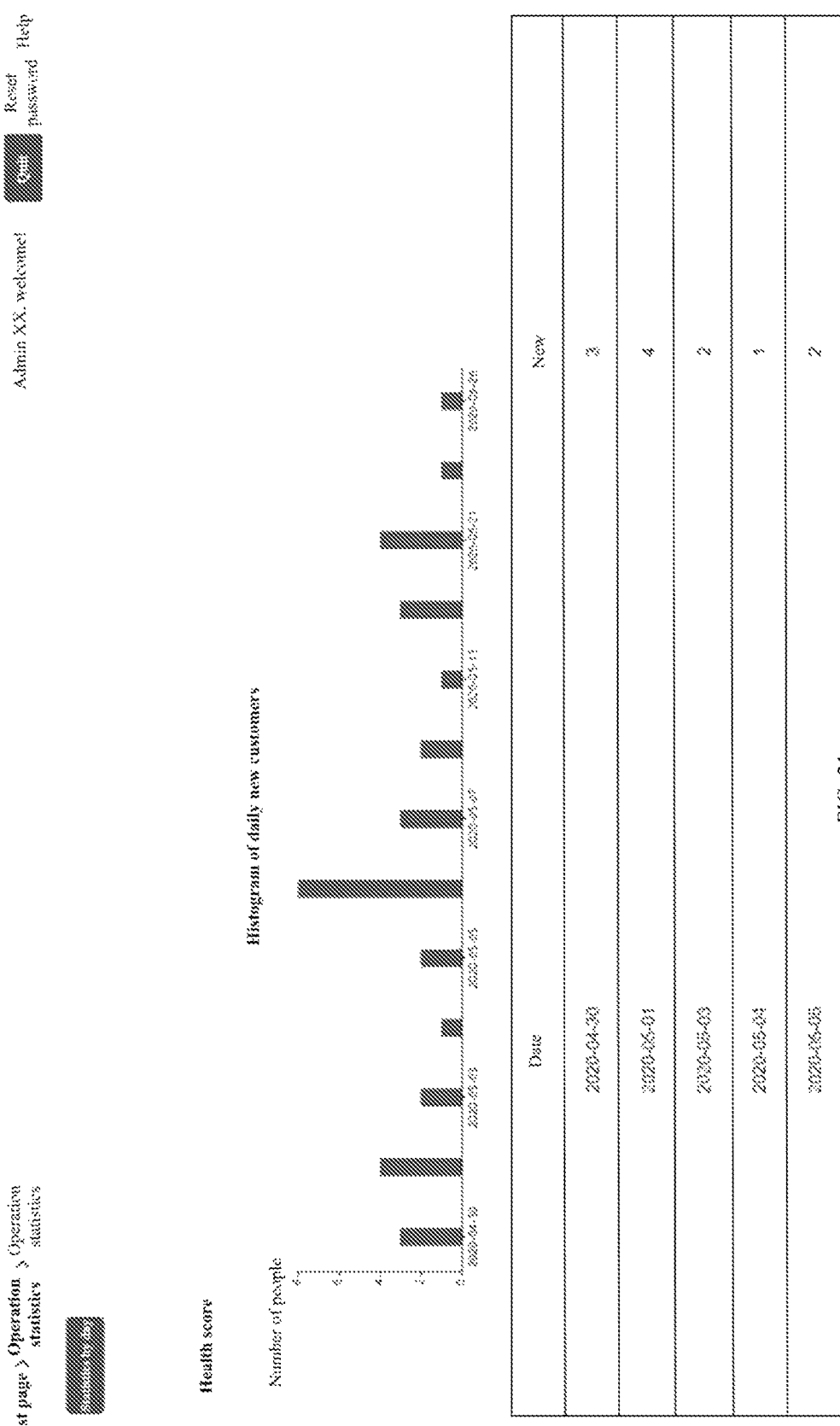
FIG. 21 shows a schematic diagram of an operation statistics subpage included by an administrator client provided by at least one embodiment of the present disclosure.

FIG. 21 shows a schematic diagram of an operation statistics subpage included by an administrator client provided by at least one embodiment of the present disclosure. For example, the medical worker administrator may view the operation data statistics result via an operation statistics subpage included by the administrator client shown in FIG. 21.

For example, the health managing method further includes: receiving, from the administrator client, medical workers' information data of generated according to a file creation operation, and supplying the medical workers' information data to the medical worker information database; in this case, the medical worker administrator may create files or update data for the medical workers.

Figure 22:
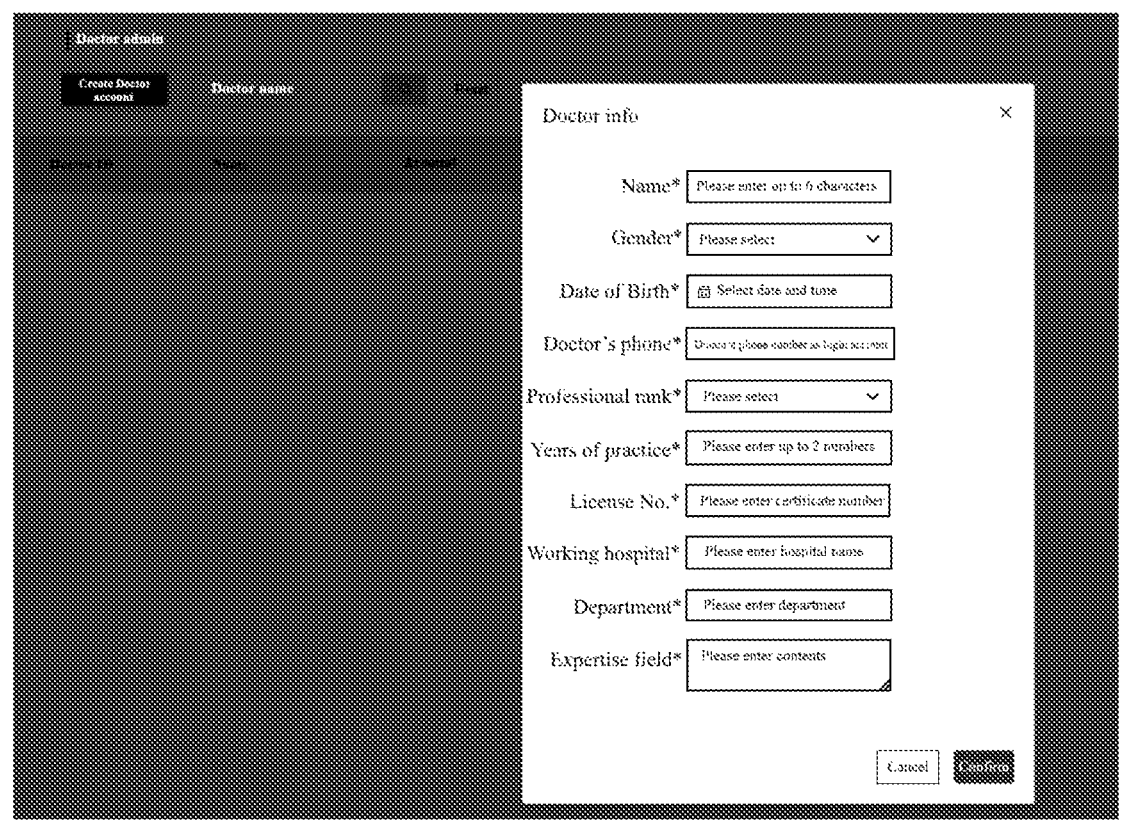

FIG. 22 shows a schematic diagram of a medical worker administration (e.g., doctor administration) subpage included by an administrator client provided by at least one embodiment of the present disclosure. For example, the medical worker administrator may input the medical workers' information data via the medical worker administration (e.g., doctor administration) subpage shown in FIG. 22 to complete file creation or data update of the medical worker.

In some examples, the health managing method provided by at least one embodiment of the present disclosure further involves interaction (e.g., data interaction) with a second administrator client. For example, in some examples, the above-described second administrator may be a health manager administrator, and the health manager may provide information consulting services for objects or formulate coping approach suggestion forms for patients with milder disease conditions. It should be noted that, the health managing method provided by at least one embodiment of the present disclosure may not involve the health manager and the second administrator (e.g., the health manager administrator). Exemplary description will be given below with reference to FIG. 23 to FIG. 29.

Figure 23:
FIG. 23 shows a schematic diagram of a customer administration subpage included by a second administrator client provided by at least one embodiment of the present disclosure.
Figure 24:
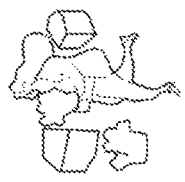
FIG. 24 shows another schematic diagram of a customer administration subpage included by a second administrator client provided by at least one embodiment of the present disclosure.
Figure 25:
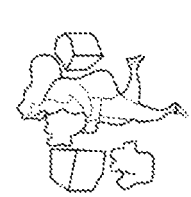
FIG. 25 shows another schematic diagram of a customer administration subpage included by a second administrator client provided by at least one embodiment of the present disclosure.
Figure 26:
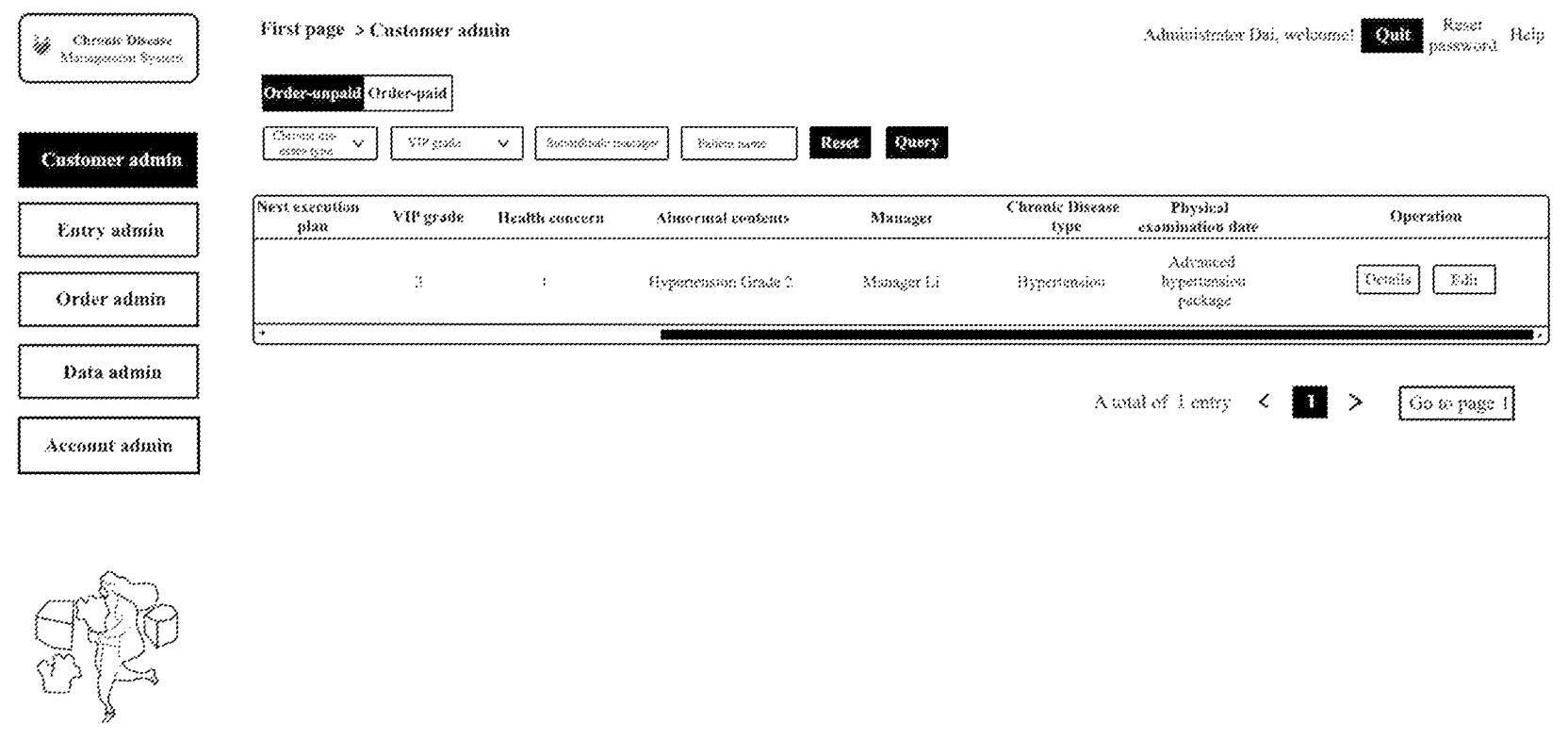

FIG. 23 shows a schematic diagram of a customer administration subpage included by a second administrator client provided by at least one embodiment of the present disclosure; FIG. 24 shows another schematic diagram of a customer administration subpage included by a second administrator client provided by at least one embodiment of the present disclosure; FIG. 25 shows another schematic diagram of a customer administration subpage included by a second administrator client provided by at least one embodiment of the present disclosure; and FIG. 26 shows another schematic diagram of a customer administration subpage included by a second administrator client provided by at least one embodiment of the present disclosure;

For example, the second administrator (e.g., the health manager administrator) may view a user's name, purchased package, and disease status, etc. via the customer administration subpage included by the second administrator client. For example, the user (customer) here refers to a user (customer) of a health managing system (e.g., a chronic disease managing system) implemented based on the health managing method provided by at least one embodiment of the present disclosure. For example, the user (customer) may be a paying user (customer) or a non-paying user (customer). For example, the second administrator (e.g., the health manager administrator) may view the paying user (customer) via an order-paid subpage of the customer administration subpage included by the second administrator client shown in FIG. 23 and FIG. 24, and may view the non-paying user (customer) via an order-unpaid subpage of the customer administration subpage included by the second administrator client shown in FIG. 23 and FIG. 24.

In some examples, at least one selected from the group consisting of the health manager and the second administrator (e.g., the health manager administrator) may follow up an order-paid user.

In some examples, at least one selected from the group consisting of the health manager and the second administrator (e.g., the health manager administrator) may view name, VIP grade, health concern, disease status, etc. of an order-unpaid user, and thus may recommend a more applicable physical examination package for the order-unpaid user.

FIG. 27 shows a schematic diagram of an order administration subpage included by a second administrator client provided by at least one embodiment of the present disclosure. For example, the second administrator (e.g., the health manager administrator) may view package purchased by an order-paid user, disease type, VIP grade, and transaction amount, etc. via the order administration subpage included by the second administrator client shown in FIG. 27.

Figure 28:
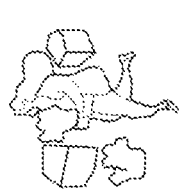
FIG. 28 shows a schematic diagram of a data administration subpage included by a second administrator client provided by at least one embodiment of the present disclosure.

FIG. 28 shows a schematic diagram of a data administration subpage included by a second administrator client provided by at least one embodiment of the present disclosure. For example, the second administrator (e.g., the health manager administrator) may view, via the data administration subpage included by the second administrator client shown in FIG. 28, the number of transactions of at least one selected from the group consisting of the health manager and the doctor (e.g., the number of objects served by at least one selected from the group consisting of the health manager and the doctor), the total transaction amount (e.g., the total amount of packages purchased the objects served by at least one selected from the group consisting of the health manager and the doctor), etc.

Figure 29:
FIG. 29 shows a schematic diagram of an account administration subpage included by a second administrator client provided by at least one embodiment of the present disclosure.

FIG. 29 shows a schematic diagram of an account administration subpage included by a second administrator client provided by at least one embodiment of the present disclosure. For example, the second administrator (e.g., the health manager administrator) may view health manager information via the account administration subpage included by the second administrator client shown in FIG. 29, and allocate right to use to the health manager (e.g., make the chronic disease managing system available or unavailable to the health manager), etc.

In some examples, health management of the object may be implemented through steps below.

Step S501: the object demanding for health management (e.g., the object putting forward a need).

Step S502: acquiring the information data of the object via the object client (e.g., the digital human body APP). For example, the information data of the object is acquired through at least one selected from the group consisting of registration information filling, questionnaire filling, and physical examination report recognition.

Step S503: intelligently recommending a physical examination package for the object based on the information data of the object, that is, outputting the physical sign examination recommendation item.

Step S504: the object undergoing offline physical examination. For example, the object may go to a hospital or a physical examination institution for physical examination. For example, if the object has completed the physical examination before generating the physical sign examination recommendation item, step S504 may be skipped.

Step S505: the object (e.g., the user) paying a fee and entering a chronic disease management process. For example, after paying the fee, the object (e.g., the user) enters the chronic disease management process.

Step S506: the administrator (e.g., the medical worker administrator) reviewing and assigning the object (e.g., assigning the object to a specified doctor). For example, in step S506, the administrator (e.g., the medical worker administrator) may review the object's information and assign an applicable medical worker (e.g., doctor) to the object.

For example, in a case where the medical worker (e.g., the doctor) did not take the order, took the order but did not operate over time (e.g., did not make a first visit over a predetermined time limit), and returned or transferred the order (cannot continue to serve the object), the object (e.g., the object's file) is automatically returned to the administrator, and the administrator again assigns an applicable medical worker (e.g., doctor) to the object.

Step S507: the medical worker (e.g., the doctor) making an initial telephone visit to the object after taking the order.

For example, the medical worker (e.g., the doctor) may communicate with the patient via telephone and acquire information of at least one selected from the group consisting of cardiovascular risk factor, target organ injuries, clinical concomitant disease, symptom, medication status, physical sign, and lifestyle, etc. For example, the medical worker (e.g., the doctor) may fill in the above-described acquired information in a first visit questionnaire, and after the first visit questionnaire is completed, the information of the first visit questionnaire will be supplied to the server. For example, the server may calculate a cardiovascular risk grade of the object according to the updated information and automatically generate a coping approach recommendation form, and then acquire (e.g., formulate) a coping approach suggestion form by adjusting the coping approach recommendation form. The medical worker (e.g., the doctor) may confirm a follow-up cycle and the coping approach suggestion form (e.g., the management plan) with the object by phone; and after the object confirms the follow-up cycle and the coping approach suggestion form (e.g., the management plan), make the follow-up cycle and the coping approach suggestion form (e.g., the management plan) effective; and the server may output the coping approach suggestion form to the object client (e.g., the digital human body APP), so that the object may view the coping approach suggestion form via the object client (e.g., the digital human body APP).

For example, after the medical worker (e.g., the doctor) completes the first visit questionnaire, the page jumps to a coping approach suggestion form adjustment page (e.g., an intervention plan or management plan writing page); the medical worker (e.g., the doctor) may formulate, for the object (e.g., the patient), a coping approach suggestion form (e.g., an intervention plan or a management plan) in a future management cycle; may respectively set a treatment goal and a follow-up cycle in the coping approach suggestion form (e.g., the intervention plan or the management plan); and may fill in a medication plan, a meal plan, an exercise plan, a hardware plan (e.g., a use plan of a physical sign monitoring device).

For example, the treatment goal may be entered in a form of text. For example, each health management package (e.g., intervention package) can only have a treatment goal set once and cannot be modified midway. For example, a follow-up date and a follow-up cycle may be generated by selecting a start date, interval time, and the number of follow-up visits.

For example, the medical worker (e.g., the doctor) may manually click to adjust (e.g., edit) the recommended exercise list generated based on the health managing method provided by at least one embodiment of the present disclosure, to acquire the exercise plan in the coping approach suggestion form. For example, a certain exercise in the recommended exercise list generated by the health managing method may be screened and replaced according to conditions (e.g., information provided by the user). For example, the medical worker may also increase or decrease duration of exercise, and add or cancel at least one item of exercise according to the object's conditions. When all exercise items on a certain day are cancelled, the day is a rest day. Conversely, exercise may also be added to a rest day.

For example, the medical worker (e.g., the doctor) may manually click to adjust (e.g., edit) the recommended diet list generated based on the health managing method provided by at least one embodiment of the present disclosure to acquire the diet plan in the coping approach suggestion form. For example, the medical worker (e.g., the doctor) may manually click to adjust (e.g., edit) meal combinations of breakfast, lunch and dinner on a specified date. For example, a certain meal in the recommended meal combinations generated by the health managing method may be screened and replaced by a replace button according to conditions (e.g., information provided by the user), and may also add or cancel categories of ingredients.

For example, the health managing system of the health managing method provided by at least one embodiment of the present disclosure may automatically capture data based on questionnaires and recommended examination items, and then strictly follow factors involved in hypertensive cardiovascular risk grading of the hypertension guideline, to automatically determine a grade (e.g., a risk grade) of the object.

For example, the health managing system of the health managing method provided by at least one embodiment of the present disclosure may automatically produce a coping approach recommendation form (e.g., personalized diet, exercise plan recommendation) according to the patient's health data. For example, the patient's health data includes the patient's physical examination report, hardware data (e.g., data output by a physical sign monitoring device), and questionnaire assessment data.

Step S508: the object (e.g., the user) starting to execute the coping approach suggestion form and waiting for a next follow-up visit.

Step S509: if the medical worker (e.g., the doctor) who executes the follow-up visit on schedule or cannot continue to administrate the patient for some reason, transferring to other medical worker (e.g., doctor) to continue the follow-up visit.

For example, during the follow-up visit, the medical worker (e.g., the doctor) communicates with the object (e.g., the user) about a management effect of a previous cycle to adjust and generate a coping approach suggestion form (e.g., a management plan) for a next cycle.

For example, after each follow-up visit, the medical worker (e.g., the doctor) may enter a health stage summary editing link (a weekly report editing link). For example, when summarizing questionnaires and coping approach suggestion forms (e.g., intervention plans) in the chronic disease managing system, the medical worker (e.g., the doctor) may fill in summary information according to the object's actual status.

Step S510: the object (e.g., the user) executing the updated coping approach suggestion form (e.g., the management plan) until an end of the management cycle.

In some examples, the health managing system (e.g., a hypertension intelligent personalized administrating system) of the health managing method provided by at least one embodiment of the present disclosure may be a platform combining a user end or object end (APP), a doctor end (a network end) and a doctor administrator end (a network end). For example, a set of pre-examination questionnaires may be formed based on the latest medical guidelines (e.g., Chinese Hypertension Prevention and Control Guidelines) and suggestions of medical staff; after the user (the object) answers the questionnaires on the APP end, the health managing system generates a personalized physical examination package applicable to the user at least based on the objects information acquired through the questionnaires. For example, the doctor administrator assigns different users to different doctors. For example, after a user chooses to purchase a package and undergoes physical examinations, the generated physical examination reports may be automatically synchronized on the doctor end, and in combination with the previous physical examination reports uploaded by the user on the app end, the health managing system will automatically generate at least one selected from the group consisting of exercise, diet, drug and health education plan, follow-up cycle and the number of follow-up visits applicable to the user's status, which is reviewed by the doctor and the doctor administrator and then output to the user end. The user performs health management according to the plan, and the doctor monitors the patient's health status in real time on the network end and follows up regularly to help the patient manage predetermined disease (e.g., hypertension) together.

In some examples, the health managing system of the health managing method provided by at least one embodiment of the present disclosure may use data collected via APP questionnaires, physical examination data, and the user's basic information filled in via APP to generate a cardiovascular risk grade (a cardiovascular risk grade for a first visit questionnaire); the doctor may further modify the data collected in the questionnaire according to an actual status during the first visit; and the health managing system may automatically calculate the user's cardiovascular risk grade according to rules of hypertension diagnosis and treatment guidelines, which, thus, can improve the doctor's work efficiency.

In some examples, the health managing system may automatically match the user's applicable diet pattern, daily intake of energy and proportions of various nutrients according to the data of the first visit questionnaire provided by the doctor, and recommend weekly recipes (including daily breakfast, lunch, dinner and snack recipes), which, thus, can recommend personalized diets according to the user's taste preferences, religious beliefs, etc., to meet nutritional needs of the hypertensive patient.

In some examples, the health managing system may automatically match the user's applicable exercise plan for hypertension (e.g., including exercise form, exercise intensity, exercise duration, and exercise frequency) according to the data of the first visit questionnaire provided by the doctor and the data of the lifestyle questionnaire provided by the object, so that the health managing system may provide an exercise plan within a management cycle, which, thus, can meet the user's own preferences and energy consumption needs.

In some examples, the health managing system may automatically recommend categories of antihypertensive drugs applicable to the user according to the data of the first visit questionnaire provided by the doctor and hypertension diagnosis and treatment guidelines, to assist the doctor in decision-making before prescribing. For example, the health managing system may automatically read information such as the current disease history and the allergy history of the current user, exclude categories of contraindicated drugs, and give priority to the most appropriate drug categories, which, thus, improves prescription efficiency of the doctor, and may also assist a physician with junior qualification to make better clinical decisions; in addition, the doctor may also choose drug categories other than those recommended by the health managing system based on experience.

In some examples, the health managing system may automatically remind the doctor to make a follow-up visit according to the management cycle set by the doctor during the first visit. during each follow-up visit, the doctor may assess contents such as the patient's clinical symptoms, medication status and lifestyle in the last management cycle by phone, flexibly adjust diet, exercise and medication plan of the next management cycle, and track changes in the user's disease condition, which, thus, can improve user compliance and initiative.

In some examples, after the follow-up visit, the health managing system automatically generates a health weekly report, performs data visualization on a management result of the user in the last cycle, and attaches the doctor's comments and guiding suggestions, which, thus, can improve stickiness between the user and the doctor as well as enthusiasm for participating in management.

Figure 30:
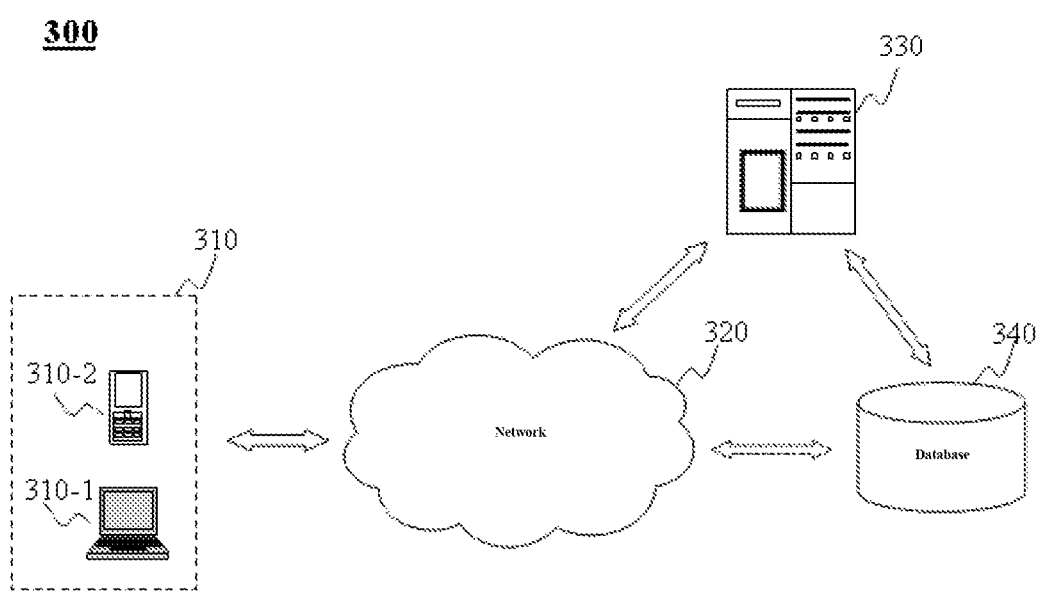
FIG. 30 shows an exemplary scene diagram of a health managing apparatus provided by at least one embodiment of the present disclosure.

FIG. 30 shows an exemplary scene diagram of a health managing apparatus (or a health managing system) provided by at least one embodiment of the present disclosure. As shown in FIG. 30, the health managing apparatus 300 may include a user terminal 310, a network 320, a server 330, and a database 340. For example, the health managing apparatus (or the health managing system) shown in FIG. 30 may be implemented according to the health managing method provided by at least one embodiment of the present disclosure.

For example, the user terminal 310 may be a computer 310-1 or a portable terminal 310-2 shown in FIG. 30. It can be understood that, the user terminal may also be any other type of electronic device that can receive, process, and display data, which may include, but is not limited to, a desktop computer, a laptop, a tablet personal computer, a smart home appliance, a wearable device, a vehicle-mounted electronic device, a medical electronic device, etc.

For example, the user terminal 310 is provided with a client. For example, the user may include an object (e.g., a patient) and a medical worker (e.g., a doctor); correspondingly, the user terminal 310 includes an object's terminal and a medical worker's terminal; the client includes an object client and a medical worker client. For example, the object client may be implemented by an APP or an applet. For example, the medical worker client may be implemented by a network end.

In some examples, the user may include at least one selected from the group consisting of a medical worker administrator and a health manager administrator; correspondingly, the user terminal 310 includes at least one selected from the group consisting of a medical worker administrator's terminal and a health manager administrator's terminal; and the client includes a medical worker administrator client and a health manager administrator client.

For example, the network 320 may be a single network, or a combination of at least two different networks. For example, the network 320 may include, but is not limited to, one or a combination of several of a local area network, a wide area network, a public network, a private network, the Internet, a mobile communication network, and the like.

For example, the server 330 may be a single server or a server group; and the respective servers in the server group is connected through a wired network or a wireless network. The wired network, for example, may perform communication by means of twisted pair, coaxial cable or optical fiber, etc.; and the wireless network, for example, may adopt communication modes such as 3G/4G/5G mobile communication network, Bluetooth, Zigbee or WiFi, etc. Types and functions of the network will not be limited here in the present disclosure. The server group may be centralized, for example, a data center, or may also be distributed. The server may be local or remote. For example, the server 330 may be a general-purpose server or a dedicated server, and may be a virtual server or a cloud server, etc.

For example, the database 340 (e.g., the object information database) may be used to store various data used, generated, and output from operations of the user terminal 310 and the server 330. The database 340 may be interconnected or communicated with the server 330 or a part of the server 330 via the network 320, or directly interconnected or communicated with the server 330, or may be interconnected or communicated with the server 330 through a combination of the above-described two modes. In some embodiments, the database 340 may be a stand-alone device. In other embodiments, the database 340 may also be integrated in at least one selected from the group consisting of the user terminal 310 and the server 340. For example, the database 340 may be provided on the user terminal 310 or on the server 340. For another example, the database 340 may also be distributed, a part of which is set on the user terminal 310, and the other part is set on the server 340.

In some examples, the client and the server may communicate with any network protocol currently known or to be researched and developed in the future such as HyperText Transfer Protocol (HTTP), and may communicate (via a communication network) and interconnect with digital data in any form or medium. Examples of communication networks include a Local Area Network ("LAN"), a Wide Area Network ("WAN"), the Internet, and an end-to-end network (e.g., an ad hoc end-to-end network), as well as any network currently known or to be researched and developed in the future.

Figure 31:
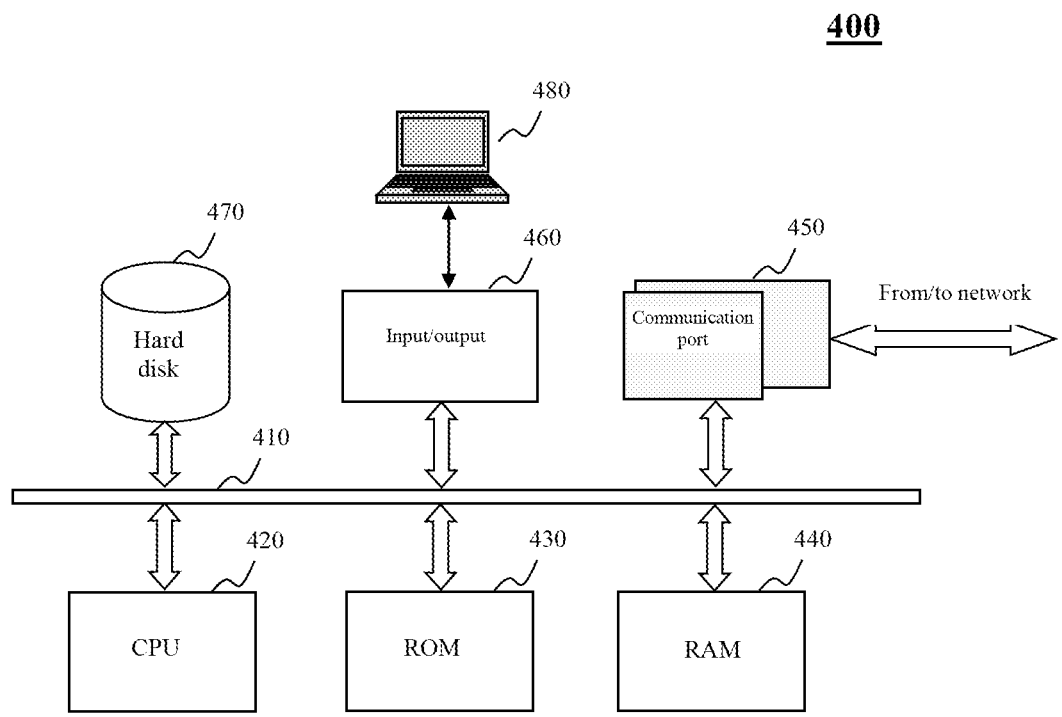
FIG. 31 shows an architecture of a computing device provided by at least one embodiment of the present disclosure.

The method according to the embodiment of the present disclosure may also be implemented with the aid of an architecture of a computing device 400 shown in FIG. 31.

FIG. 31 shows the architecture of the computing device 400 provided by at least one embodiment of the present disclosure. As shown in FIG. 31, the computing device 400 may include a bus 410, one or at least two processors such as a CPU 420, a Read Only Memory (ROM) 430, a Random Access Memory (RAM) 440, a communication port 450 connected to a network, an input/output component 460, and a hard disk 470, etc. A storage device (e.g., the ROM 430 or the hard disk 470) in the computing device 400 may store instructions corresponding to the health managing method provided by at least one embodiment of the present disclosure and various related data or files. The computing device 400 may also include a human-machine user interface 480. Of course, the architecture shown in FIG. 31 is only exemplary; and when implementing different devices, one or at least two components in the computing device shown in FIG. 31 may be omitted according to actual needs.

Figure 32:
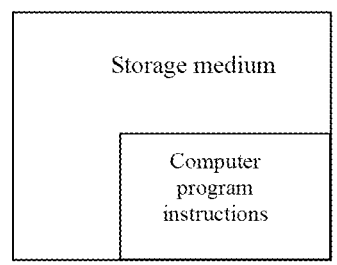
FIG. 32 shows an exemplary block diagram of a storage medium provided by at least one embodiment of the present disclosure.

At least one embodiment of the present disclosure further provides a storage medium (e.g., a non-transitory storage medium). FIG. 32 is an exemplary block diagram of a storage medium provided by at least one embodiment of the present disclosure. As shown in FIG. 32, the storage medium includes stored computer program instructions. When run by a processor, the computer program instructions execute any health managing method provided by at least one embodiment of the present disclosure. For example, the storage medium may improve work efficiency of medical workers.

For example, the storage medium may have various forms, including a tangible storage medium, a carrier wave medium, or a physical transmission medium. A stable storage medium may include: an optical disk or a magnetic disk, and other storage system used in a computer or a similar device that can implement the system components described in the diagrams. An unstable storage medium may include a dynamic memory, for example, a main memory of a computer platform. A tangible transmission medium may include a coaxial cable, a copper cable, and an optical fiber, for example, lines that form a bus inside a computer system. The carrier wave transmission medium may transmit electric signals, electromagnetic signals, acoustic wave signals, or light wave signals, etc. These signals may be generated by radio frequency or infrared data communication methods. A common storage medium (e.g., a computer-readable medium) includes a hard disk, a floppy disk, a magnetic tape, and any other magnetic medium; a Compact Disc Read-Only Memory (CD-ROM), a Digital Versatile Disk (DVD), a Digital Versatile Disk Read-Only Memory (DVD- ROM), and any other optical medium; a punch card, and any other physical storage medium containing a pinhole pattern; a Random Access Memory (RAM), a Programmable Read-Only Memory (PROM), an Electrical Programmable Read Only Memory (EPROM), a FLASH-EPROM, and any other memory chip or tape; a carrier wave and a cable for transmitting data or instructions, or a connecting device for transmitting carrier waves, and any other data that can be read by using computer program instructions (e.g., program codes) and/or computers.

The computer program instructions (e.g., the program codes) for executing the operations according to the present disclosure may be written in one or more programming languages or a combination thereof. The above-described programming languages include, but are not limited to, object-oriented programming languages such as Java, Smalltalk, C++, and also include conventional procedural programming languages such as "C" language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a Local Area Network (LAN) or a Wide Area Network (WAN), or the connection may be made to an external computer (for example, through the Internet using an Internet Service Provider).

Other embodiments of the present disclosure will readily occur to those skilled in the art after considering the specification and practicing the disclosure disclosed herein. This disclosure is intended to cover any modification, use or adaptation of this disclosure, which follows the general principles of this disclosure and includes common knowledge or conventional technical means in the technical field not disclosed in this disclosure. The specification and examples are to be regarded as exemplary only, with the true scope and spirit of the disclosure being indicated by the following claims.

It should be understood that the present disclosure is not limited to the precise structure described above and shown in the drawings, and various modifications and changes can be made without departing from its scope. The scope of this disclosure is limited only by the appended claims.

What is claimed is:

1. A health managing method, comprising:
    connecting to an object information database, and acquiring at least one piece of physical sign data of an object from the object information database, wherein the at least one piece of physical sign data includes an examination result of at least one physical sign examination item in which the object participates;
    automatically determining at least a health management influencing factor at least based on the at least one piece of physical sign data; and
    automatically generating a coping approach recommendation form at least based on the health management influencing factor, wherein the coping approach recommendation form is used to generate a coping approach suggestion form;
    wherein the method further comprises:
    receiving, from a client, basic information data of the object, which is generated according to a basic information filling operation, and questionnaire assessment data of the object, which is generated according to a health questionnaire filling operation,
    storing the basic information data of the object and the questionnaire assessment data of the object to the object information database, and
    automatically generating a physical sign examination recommendation item based on at least one selected from the group consisting of the basic information data of the object and the questionnaire assessment data of the object, wherein the physical sign examination recommendation item is used for recommending to the object to participate the physical sign examination recommendation item in advance, the physical sign examination recommendation item comprises physical sign examination items for a chronic disease that the object is currently seeking medical consultation for and a physical sign examination item for other related diseases that the object may have;
    receiving, from the client, physical sign examination report data of the object, which is generated according to a physical sign examination report uploading operation; and
    acquiring, from the physical sign examination report data of the object, physical sign data included in the examination result of the physical sign examination item in which the object participates,
    wherein the physical sign data is structured data, and the object information database is a relational database, the physical sign examination report data of the object comprises a page of the physical sign examination report, the page of the physical sign examination report is obtained by taking a photo or scanning a paper physical sign examination report, or obtained from an information platform of a medical institution and a physical examination institution,
    acquiring, from the physical sign examination report data of the object, physical sign data included in the examination result of the physical sign examination item in which the object participates, comprises:
    performing Optical Character Recognition (OCR) on the page of the physical sign examination report to obtain character information;
    structuring the character information to convert the character information from unstructured data to structured data, to obtain the structured physical sign data; and
    storing the structured physical sign data to the object information database;
    wherein the basic information data of the object includes:
    at least one selected from the group consisting of a current disease history of the object, a family disease history of the object, past disease information of the object, a surgical history of the object, a medication history of the object, an allergy history of the object, and lifestyle information of the object, as well as a gender of the object, a birth date of the object, a height of the object, and a weight of the object.

2. The health managing method according to claim 1, further comprising:
    receiving, from the client, a review result, generated according to an information review operation, of at least one item of the basic information data of the object and the questionnaire assessment data of the object; and
    updating, in response to an omission or error in at least one item of the basic information data of the object and the questionnaire assessment data of the object, at least one item of the basic information data of the object and the questionnaire assessment data of the object in the object information database based on the review result.

3. The health managing method according to claim 1, wherein the physical sign examination report data of the object includes report data of a physical sign examination in which the object participated previously;

the physical sign data included in the examination result of the physical sign examination item in which the object participates includes the physical sign data included in the examination result of the physical sign examination item in which the object previously participated; and the health managing method further comprises:

supplying the physical sign data included in the examination result of the physical sign examination item in which the object previously participated to the object information database; and the automatically generating a physical sign examination recommendation item based on at least one selected from the group consisting of the basic information data of the object and the questionnaire assessment data of the object includes:

automatically generating the physical sign examination recommendation item based on at least one selected from the group consisting of the basic information data of the object and based on the questionnaire assessment data of the object and the physical sign data included in the examination result of the physical sign examination item in which the object previously participated.

4. The health managing method according to claim 1, wherein the physical sign examination report data of the object includes data of a physical sign examination report of a physical sign examination item in which the object actually participates among automatically generated physical sign examination recommendation items;

the physical sign data included in the examination result of the physical sign examination item in which the object participates includes the physical sign data included in the physical sign examination report of the physical sign examination item in which the object actually participates among the automatically generated physical sign examination recommendation items; and the health managing method further includes:

supplying the physical sign data included in the physical sign examination report of the physical sign examination item in which the object actually participates among the automatically generated physical sign examination recommendation items to the object information database.

5. The health managing method according to claim 1, wherein the automatically generating a coping approach recommendation form at least based on the health management influencing factor includes:

automatically determining a grade of the object based on the health management influencing factor, and automatically generating the coping approach recommendation form based on at least one selected from the group consisting of the grade of the object and the health management influencing factor; and the coping approach recommendation form includes at least one selected from the group consisting of a recommended drug list, a recommended diet plan list, a recommended exercise plan list, and a recommended management cycle.

6. The health managing method according to claim 5, further comprising:

connecting to the object information database, and acquiring a drug contraindication of the object from the object information database, wherein the health management influencing factor includes a concomitant clinical disease factor;

the automatically generating a coping approach recommendation form includes:

automatically generating the recommended drug list; and the automatically generating the recommended drug list includes:

connecting to a drug information database to acquire an available drug list;

eliminating inapplicable drugs in the available drug list based on the concomitant clinical disease factor and the drug contraindication of the object, to acquire an applicable drug list; and determining the recommended drug list from the applicable drug list based on the grade of the object.

7. The health managing method according to claim 5, further comprising:

connecting to the object information database, and acquiring a gender of the object, an age of the object, a height of the object, a weight of the object, a diet preference of the object or a dietary taboo of the object from the object information database; and automatically generating the recommended diet plan list at least based on the gender of the object, the age of the object, the height of the object, the weight of the object, the diet preference of the object, the dietary taboo of the object or the health management influencing factor or any combination thereof.

8. The health managing method according to claim 5, further comprising:

connecting to the object information database, and acquiring an exercise preference of the object from the object information database; and automatically generating the recommended exercise list at least based on the grade of the object, the exercise preference of the object and a predetermined exercise principle.

9. The health managing method according to claim 5, further comprising:

connecting to the object information database, and acquiring a gender of the object, an age of the object, a height of the object, a weight of the object, lifestyle information of the object or a family disease history of the object from the object information database, wherein the automatically determining at least the health management influencing factor at least based on the at least one piece of physical sign data includes:

automatically determining the health management influencing factor at least based on the gender of the object, the age of the object, the height of the object, the weight of the object, the lifestyle information of the object or the family disease history of the object as well as the at least one piece of physical sign data; and the health management influencing factor include at least one selected from the group consisting of a risk factor of a predetermined disease, target organ injury of a predetermined disease, and a concomitant clinical disease.

10. The health managing method according to claim 5, wherein the automatically determining the grade of the object based on the health management influencing factor includes:

determining a temporary grade of the object based on a core factor in the health management influencing factor, and determining the grade of the object based on the temporary grade of the object and other factor than the core factor in the health management influencing factor; and the health management influencing factor include at least one selected from the group consisting of a risk factor of a predetermined disease, target organ injury of a predetermined disease, and a concomitant clinical disease.

11. The health managing method according to claim 5, further comprising:

connecting, in response to that a number of pieces of physical sign data satisfying the predetermined time condition is less than a required number of pieces of physical sign data, to the object information database, and acquiring past disease information of the object from the object information database;

wherein the acquiring past disease information of the object from the object information database includes:

acquiring at least one piece of physical sign data of the object that satisfies a predetermined time condition from the object information database.

12. The health managing method according to claim 1, further comprising:

receiving, from the client, coping approach recommendation form adjustment data generated according to a coping approach recommendation form adjustment operation; and adjusting the coping approach recommendation form based on the coping approach recommendation form adjustment data, to generate the coping approach suggestion form, wherein the coping approach suggestion form includes at least one selected from the group consisting of a drug regimen, a diet plan, an exercise plan, and a management cycle.

13. The health managing method according to claim 12, further comprising:

receiving, from the client or a physical sign monitoring device used by the object, at least one piece of updated physical sign data of the object that is generated by the physical sign monitoring device used by the object; and outputting, in response to the updated physical sign data being abnormal, a first alarm instruction.

14. The health managing method according to claim 12, further comprising:

receiving, from the client, execution confirmation data generated according to a coping approach suggestion form execution confirmation operation; and outputting, in response to not receiving the execution confirmation data from the client within a predetermined time period, a second alarm instruction.

15. The health managing method according to claim 12, further comprising:

receiving, from the client, the coping approach suggestion form adjustment data generated according to the coping approach suggestion form adjustment operation;

updating the coping approach recommendation form based on the coping approach suggestion form adjustment data;

receiving, from the client, visit data generated according to a visit status filling operation; and automatically generating a health stage summary at least based on the visit data.

16. A computing device, comprising:

one or more processors;

one or more storage devices on which computer program instructions are stored, wherein when run by the one or more processors, the computer program instructions execute a health managing method, comprising:

connecting to an object information database, and acquiring at least one piece of physical sign data of an object from the object information database, wherein the at least one piece of physical sign data includes an examination result of at least one physical sign examination item in which the object participates;

automatically determining at least a health management influencing factor at least based on the at least one piece of physical sign data; and automatically generating a coping approach recommendation form at least based on the health management influencing factor, wherein the coping approach recommendation form is used to generate a coping approach suggestion form;

receiving, from a client, basic information data of the object, which is generated according to a basic information filling operation, and questionnaire assessment data of the object, which is generated according to a health questionnaire filling operation, storing the basic information data of the object and the questionnaire assessment data of the object to the object information database, and automatically generating a physical sign examination recommendation item based on at least one selected from the group consisting of the basic information data of the object and the questionnaire assessment data of the object, wherein the physical sign examination recommendation item is used for recommending to the object to participate the physical sign examination recommendation item in advance, the physical sign examination recommendation item comprises physical sign examination items for a chronic disease that the object is currently seeking medical consultation for and a physical sign examination item for other related diseases that the object may have;

receiving, from the client, physical sign examination report data of the object, which is generated according to a physical sign examination report uploading operation; and acquiring, from the physical sign examination report data of the object, physical sign data included in the examination result of the physical sign examination item in which the object participates, wherein the physical sign data is structured data, and the object information database is a relational database, the physical sign examination report data of the object comprises a page of the physical sign examination report, the page of the physical sign examination report is obtained by taking a photo or scanning a paper physical sign examination report, or obtained from an information platform of a medical institution and a physical examination institution, acquiring, from the physical sign examination report data of the object, physical sign data included in the examination result of the physical sign examination item in which the object participates, comprises:

performing Optical Character Recognition (OCR) on the page of the physical sign examination report to obtain character information;

structuring the character information to convert the character information from unstructured data to structured data, to obtain the structured physical sign data; and storing the structured physical sign data to the object information database;

wherein the basic information data of the object includes: at least one selected from the group consisting of a current disease history of the object, a family disease history of the object, past disease information of the object, a surgical history of the object, a medication history of the object, an allergy history of the object, and lifestyle information of the object, as well as a gender of the object, a birth date of the object, a height of the object, and a weight of the object.

17. A non-transitory storage medium, comprising stored computer program instructions, wherein when run by a processor, the stored computer program instructions execute a health managing method, comprising:

connecting to an object information database, and acquiring at least one piece of physical sign data of an object from the object information database, wherein the at least one piece of physical sign data includes an examination result of at least one physical sign examination item in which the object participates;

automatically determining at least a health management influencing factor at least based on the at least one piece of physical sign data; and automatically generating a coping approach recommendation form at least based on the health management influencing factor, wherein the coping approach recommendation form is used to generate a coping approach suggestion form;

receiving, from a client, basic information data of the object, which is generated according to a basic information filling operation, and questionnaire assessment data of the object, which is generated according to a health questionnaire filling operation, storing the basic information data of the object and the questionnaire assessment data of the object to the object information database, and automatically generating a physical sign examination recommendation item based on at least one selected from the group consisting of the basic information data of the object and the questionnaire assessment data of the object, wherein the physical sign examination recommendation item is used for recommending to the object to participate the physical sign examination recommendation item in advance, the physical sign examination recommendation item comprises physical sign examination items for a chronic disease that the object is currently seeking medical consultation for and a physical sign examination item for other related diseases that the object may have;

receiving, from the client, physical sign examination report data of the object, which is generated according to a physical sign examination report uploading operation; and acquiring, from the physical sign examination report data of the object, physical sign data included in the examination result of the physical sign examination item in which the object participates, wherein the physical sign data is structured data, and the object information database is a relational database, the physical sign examination report data of the object comprises a page of the physical sign examination report, the page of the physical sign examination report is obtained by taking a photo or scanning a paper physical sign examination report, or obtained from an information platform of a medical institution and a physical examination institution, acquiring, from the physical sign examination report data of the object, physical sign data included in the examination result of the physical sign examination item in which the object participates, comprises:

performing Optical Character Recognition (OCR) on the page of the physical sign examination report to obtain character information;

structuring the character information to convert the character information from unstructured data to structured data, to obtain the structured physical sign data; and storing the structured physical sign data to the object information database;

wherein the basic information data of the object includes: at least one selected from the group consisting of a current disease history of the object, a family disease history of the object, past disease information of the object, a surgical history of the object, a medication history of the object, an allergy history of the object, and lifestyle information of the object, as well as a gender of the object, a birth date of the object, a height of the object, and a weight of the object.

* * * * *